US011333649B2

(12) United States Patent
Lalović

(10) Patent No.: US 11,333,649 B2
(45) Date of Patent: May 17, 2022

(54) HYPERSPECTRAL SENSING SYSTEM

(71) Applicant: Flying Gybe Inc., Corvallis, OR (US)

(72) Inventor: Ivan Lalović, Portland, OR (US)

(73) Assignee: Flying Gybe Inc., Corvallis, OR (US)

( * ) Notice: Subject to any disclaimer, the term of this patent is extended or adjusted under 35 U.S.C. 154(b) by 0 days.

(21) Appl. No.: 16/988,562

(22) Filed: Aug. 7, 2020

(65) Prior Publication Data

US 2020/0371081 A1 Nov. 26, 2020

Related U.S. Application Data

(62) Division of application No. 16/366,635, filed on Mar. 27, 2019, now Pat. No. 10,794,888.

(60) Provisional application No. 62/648,779, filed on Mar. 27, 2018.

(51) Int. Cl.
*G01J 3/02* (2006.01)
*G01J 3/04* (2006.01)
*G01N 33/18* (2006.01)
*G01N 21/25* (2006.01)
*G02B 5/30* (2006.01)
*G02B 26/04* (2006.01)

(52) U.S. Cl.
CPC ............ *G01N 33/18* (2013.01); *G01J 3/0208* (2013.01); *G01J 3/0224* (2013.01); *G01J 3/04* (2013.01); *G01N 21/25* (2013.01); *G01J 3/0291* (2013.01); *G02B 5/3025* (2013.01); *G02B 26/04* (2013.01)

(58) Field of Classification Search
CPC ...... G01J 3/0208; G01J 3/0224; G01J 3/0289; G01J 3/04; G01J 3/42; G01N 21/25; G01N 21/31; G01N 33/18; G02B 26/04; G02B 5/3025
See application file for complete search history.

(56) References Cited

U.S. PATENT DOCUMENTS

| | | | | |
|---|---|---|---|---|
| 4,060,327 A * | 11/1977 | Jacobowitz | ............... | G01J 3/10 356/328 |
| 2004/0133086 A1* | 7/2004 | Ciurczak | ............... | A61B 5/1455 600/322 |
| 2008/0094623 A1* | 4/2008 | Schuurmans | ............. | G01J 3/04 356/306 |
| 2015/0308891 A1* | 10/2015 | Gotsmann | ................. | G01J 3/28 356/326 |
| 2016/0138974 A1* | 5/2016 | Silny | ..................... | G01J 3/0232 356/328 |

(Continued)

OTHER PUBLICATIONS

Ramon et al., "Modeling polarized radiative transfer in the ocean-atmosphere system with the GPU-accelerated SMART-G Monte Carlo code", Journal of Quantitative Spectroscopy & Radiative Transfer, Oct. 11, 2018, pp. 89-107, vols. 222-223.

*Primary Examiner* — Hina F Ayub
(74) *Attorney, Agent, or Firm* — Kolitch Romano LLP

(57) ABSTRACT

A hyperspectral sensing device may include an optical collector configured to collect light and to transfer the collected light to a sensor having spectral resolution sufficient for sensing hyperspectral data. In some examples, the sensor comprises a compact spectrometer. The device further comprises a power supply, an electronics module, and an input/output hub enabling the device to transmit acquired data (e.g., to a remote server). In some examples, a plurality of hyperspectral sensing devices are deployed as a network to acquire data over a relatively large area.

19 Claims, 19 Drawing Sheets

(56) References Cited

U.S. PATENT DOCUMENTS

2016/0356646 A1 12/2016 Wiegand
2019/0159663 A1* 5/2019 Krstajic ............... A61B 5/0084

* cited by examiner

HYPERSPECTRAL SENSING SYSTEM

CROSS-REFERENCES

The following related applications and materials are incorporated herein, in their entireties, for all purposes: U.S. Provisional Patent Application Ser. No. 62/648,779, filed Mar. 27, 2018, and U.S. patent application Ser. No. 16/366,635, filed Mar. 27, 2019.

FIELD

This disclosure relates to systems and methods for hyperspectral sensing.

INTRODUCTION

Optical characteristics of aquatic, terrestrial, and atmospheric environments may be measured to detect the presence and/or abundance of various substances. For example, the wavelength-dependent intensity of light reflected from or absorbed within oceans, lakes, and other bodies of water may be monitored over time to quantify gradual or sudden changes in concentrations of sediment and/or biological matter. Similarly, optical absorption and scattering from land may be monitored to obtain spatial and/or temporal distributions of vegetation, minerals, and/or other substances.

In many cases, much of the useful information contained in this optical data involves wavelength- or frequency-dependent characteristics of the measured light. Systems configured to measure light at a high spectral resolution are therefore desirable. A hyperspectral sensor, which can measure the spectrum of light at each spatial pixel in a region of interest, would provide a large amount of high-resolution data. However, known hyperspectral sensing systems suffer from a number of drawbacks. For example, known systems are typically limited to a single mode of deployment (e.g., above-water deployment only, underwater deployment only, etc.), and are unsuitable for autonomous deployment due to factors such as size, cost, power requirements, and sensitivity to vibration. Accordingly, there is a need for hyperspectral sensing systems configured for field use in water-quality assessment, remote sensing, and/or other similar applications.

SUMMARY

The present disclosure provides systems, apparatuses, and methods relating to hyperspectral sensing.

In some embodiments, an autonomous optical sensing device may include a first spectrometer including a sensing element; an optical system configured to direct ambient light incident from a first direction onto the sensing element of the first spectrometer; and a first controller coupled to the first spectrometer and configured to automatically trigger data acquisition by the first spectrometer at selected intervals; wherein the first spectrometer and the optical system are at least partially encased in a common housing.

In some embodiments, an autonomous hyperspectral sensing device may include a housing having a first aperture configured to receive ambient light from a first direction; a spectrometer disposed within the housing, the spectrometer including a sensing element, a spectrometer body having an input slit, and an optical element disposed within the spectrometer body and configured to direct light received through the input slit toward the sensing element in wavelength-dependent directions; an optical system disposed within the housing and configured to direct light received through the first aperture to the input slit; and an electronic controller disposed within the housing and configured to automatically trigger data acquisition by the spectrometer.

Features, functions, and advantages may be achieved independently in various embodiments of the present disclosure, or may be combined in yet other embodiments, further details of which can be seen with reference to the following description and drawings.

DETAILED DESCRIPTION

Figure 1:
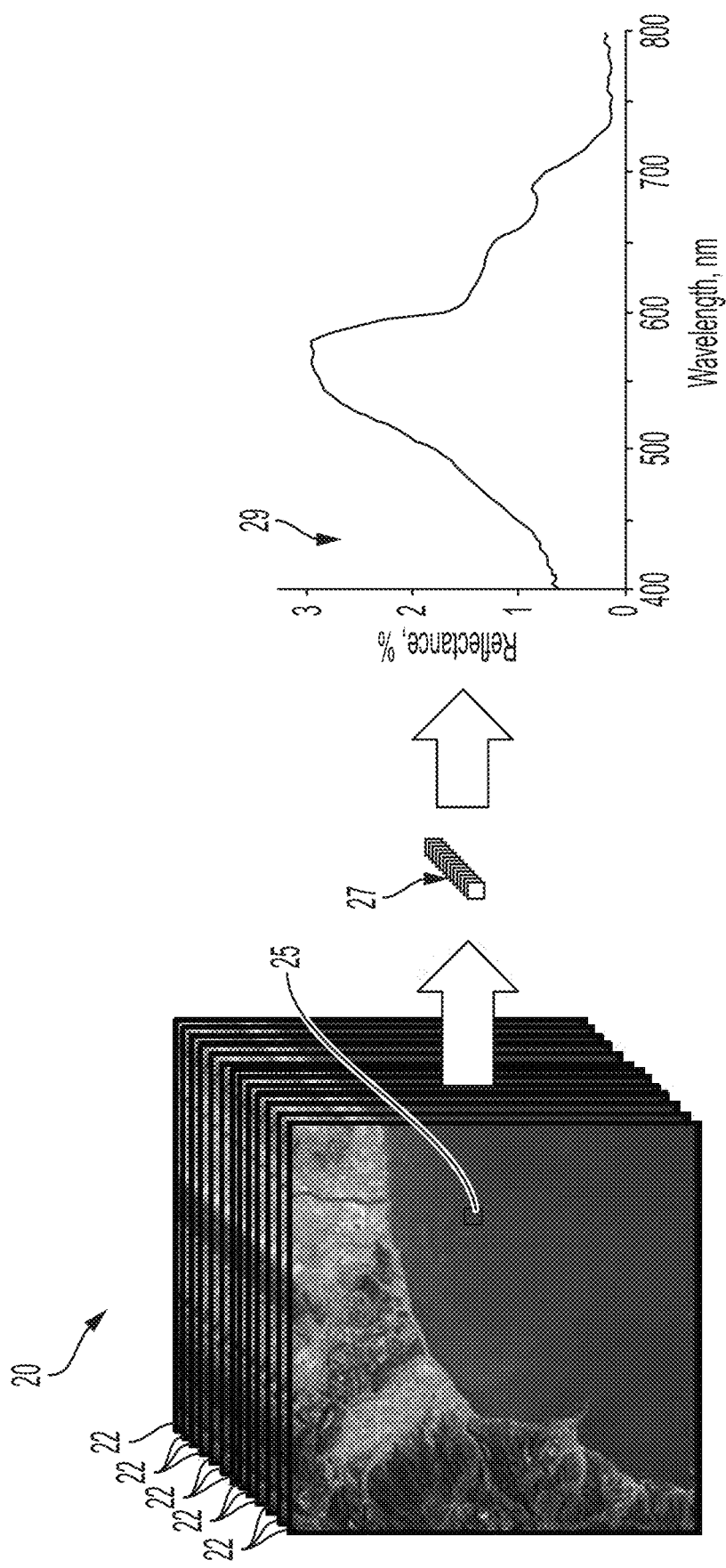
FIG. 1 is a schematic depiction of an illustrative hyperspectral image in accordance with aspects of the present teachings.

Various aspects and examples of a hyperspectral sensing system, as well as related methods, are described below and illustrated in the associated drawings. Unless otherwise specified, a hyperspectral sensing system in accordance with the present teachings, and/or its various components, may contain at least one of the structures, components, functionalities, and/or variations described, illustrated, and/or incorporated herein. Furthermore, unless specifically excluded, the process steps, structures, components, functionalities, and/or variations described, illustrated, and/or incorporated herein in connection with the present teachings may be included in other similar devices and methods, including being interchangeable between disclosed embodiments. The following description of various examples is merely illustrative in nature and is in no way intended to limit the disclosure, its application, or uses. Additionally, the advantages provided by the examples and embodiments described below are illustrative in nature and not all examples and embodiments provide the same advantages or the same degree of advantages.

This Detailed Description includes the following sections, which follow immediately below: (1) Definitions; (2) Overview; (3) Examples, Components, and Alternatives; (4) Advantages, Features, and Benefits; and (5) Conclusion. The Examples, Components, and Alternatives section is further divided into subsections A through M, each of which is labeled accordingly.

Definitions

The following definitions apply herein, unless otherwise indicated.

"Substantially" means to be more-or-less conforming to the particular dimension, range, shape, concept, or other aspect modified by the term, such that a feature or component need not conform exactly. For example, a "substantially cylindrical" object means that the object resembles a cylinder, but may have one or more deviations from a true cylinder.

"Comprising," "including," and "having" (and conjugations thereof) are used interchangeably to mean including but not necessarily limited to, and are open-ended terms not intended to exclude additional, unrecited elements or method steps.

Terms such as "first", "second", and "third" are used to distinguish or identify various members of a group, or the like, and are not intended to show serial or numerical limitation.

"AKA" means "also known as," and may be used to indicate an alternative or corresponding term for a given element or elements.

"Coupled" means connected, either permanently or releasably, whether directly or indirectly through intervening components.

"Processing logic" means any suitable device(s) or hardware configured to process data by performing one or more logical and/or arithmetic operations (e.g., executing coded instructions). For example, processing logic may include one or more processors (e.g., central processing units (CPUs) and/or graphics processing units (GPUs)), microprocessors, clusters of processing cores, FPGAs (field-programmable gate arrays), artificial intelligence (AI) accelerators, digital signal processors (DSPs), and/or any other suitable combination of logic hardware.

In this disclosure, one or more publications, patents, and/or patent applications may be incorporated by reference. However, such material is only incorporated to the extent that no conflict exists between the incorporated material and the statements and drawings set forth herein. In the event of any such conflict, including any conflict in terminology, the present disclosure is controlling.

Overview

In general, a hyperspectral sensing system in accordance with aspects of the present teachings is configured to obtain hyperspectral data while deployed in the field (e.g., adjacent a body of water, underwater, on an aerial vehicle, and/or the like). Typically, the hyperspectral sensing system includes a sensor configured to measure a spectrum of light with a high spectral resolution, along with one or more optical assemblies configured to direct light to the sensor. For example, the system may comprise one or more compact spectrometers (AKA miniature spectrometers) and suitable optics.

Hyperspectral data generally comprises an image composed of one or more spatial pixels, with high-resolution spectral information (e.g., wavelength-dependent or frequency-dependent information) associated with each pixel. The spectral information may include a measured light level (e.g., brightness, energy, power, and/or intensity of light) in each of a plurality of narrow, adjacent spectral bands. Hyperspectral data may be represented by a hyperspectral image, which may be thought of as a three-dimensional image or hyperspectral cube having two spatial dimensions and one spectral dimension. FIG. 1 depicts an illustrative hyperspectral image 20 comprising a plurality of two-dimensional images 22 of a coastal region, wherein each two-dimensional image corresponds to a detected level of light within a respective spectral band. In other words, each pixel 25 of one of the two-dimensional images 22 is associated with a level of light detected within the spectral band associated with that two-dimensional image.

Accordingly, as shown schematically in FIG. 1, a set 27 of pixels 25 corresponding to a same location in each of the two-dimensional images comprises a spectrum of detected light levels for the corresponding location across all spectral bands in hyperspectral image 20. The spectrum associated with set 27 may be illustrated as a plot 29 depicting measured light level (e.g., percentage of light reflected) as a function of wavelength for the location associated with the selected pixel 25. Hyperspectral image 20 comprises such a spectrum for each spatial pixel in the image.

For simplicity, only a few two-dimensional images 22 are depicted in FIG. 1, and therefore the depicted hyperspectral image 20 comprises only a few spectral bands. Typically, however, hyperspectral images include light levels associated with at least tens or hundreds of adjacent and/or narrowly spaced spectral bands, such that the spectrum associated with a given pixel across the plurality of two-dimensional images (e.g., a spectrum like that depicted in plot 29) is, to good approximation, continuous.

A hyperspectral sensing system may be referred to as a hyperspectral imaging system and/or a hyperspectral imager. As discussed below, the hyperspectral sensing system of the present disclosure is configured to log (e.g., record) hyperspectral data and therefore may also be referred to as a hyperspectral logger, hyperspectral logging system, hyperspectral logging radiometer, and/or optical data logger.

A hyperspectral sensing system in accordance with aspects of the present teachings is typically well suited for use in water-quality assessments, remote sensing, underwater deployment, and/or other field settings. For example, the system may comprise one or more devices that are small in size, lightweight, suitable for use in or adjacent water, relatively insensitive to vibration, and/or configured to acquire data without careful alignment and/or frequent calibration. In some examples, a hyperspectral sensing system comprises a network of hyperspectral sensing devices distributed in a suitable location and configured to store and/or transmit sensed data.

A hyperspectral sensing system in accordance with aspects of the present teachings may be used to acquire hyperspectral data in a variety of deployment modalities. For example, the system typically has a low physical volume and a low weight and is therefore suitable for aerial deployment, e.g., on an airplane, unmanned aerial vehicle, weather balloon, and/or the like. In some examples, the system may also be deployed underwater, e.g., on a watercraft, buoy, unmanned underwater vehicle, manually operated by a diver, and so on. Additionally, or alternatively, the system may be deployed on the ground, adjacent a body of water, and/or in any other suitable location. In some examples, the system is configured to simultaneously measure light incident from multiple directions, e.g., from the sky and from a body of water.

In some examples, the system is used to acquire data from a discrete sample (e.g., a sample of water and/or another fluid) collected by a profiling system (e.g., a rosette comprising an array of Niskin bottles, Scotty bottles, and/or the like, and optionally including sensors such as CTD sensors). In some examples, a sample of fluid is collected by a flow-through system configured to pump fluid into a sample chamber, and the system acquires data from the sample within the sample chamber. These capabilities are discussed further below.

EXAMPLES, COMPONENTS, AND ALTERNATIVES

The following sections describe selected aspects of exemplary hyperspectral sensing systems as well as related systems and/or methods. The examples in these sections are intended for illustration and should not be interpreted as limiting the scope of the present disclosure. Each section may include one or more distinct embodiments or examples, and/or contextual or related information, function, and/or structure.

A. Illustrative Hyperspectral Sensing Device

Figure 2:
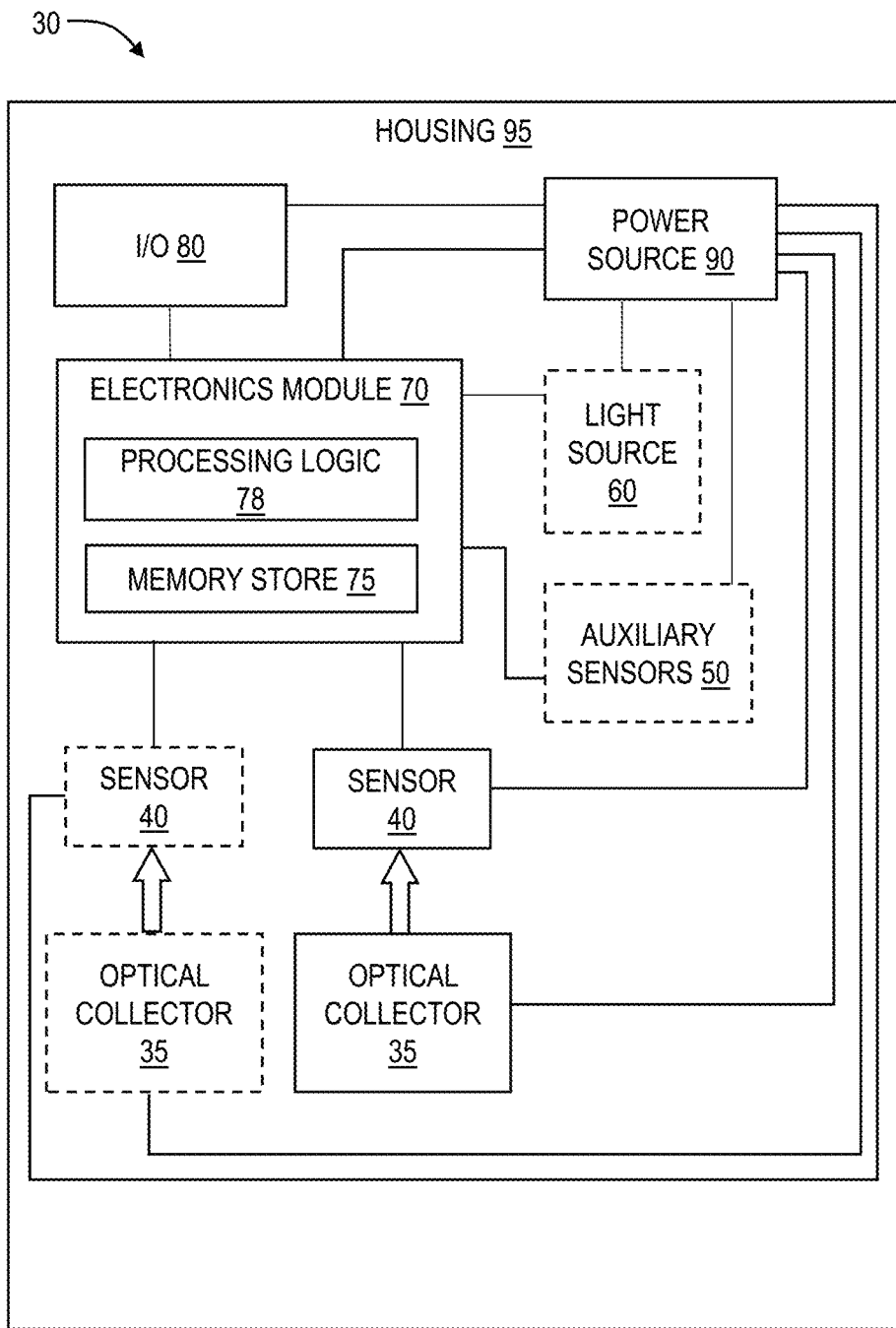
FIG. 2 is a schematic depiction of an illustrative hyperspectral sensing device in accordance with aspects of the present teachings.

With reference to FIG. 2, this section describes an illustrative hyperspectral sensing device 30. Device 30 is an example of the hyperspectral sensing systems described above.

As shown in FIG. 2, which is a schematic depiction of device 30, the device includes an optical collector 35 configured to collect light from a sample spatial region. The sample region may include a landmass, a body of water, a portion of the atmosphere, and/or any other suitable area or object of interest.

Collector 35 is further configured to transfer the collected light from the sample region to a sensor 40. Transferring the light to sensor 40 typically includes steering the light toward the sensor and may further include minimizing optical distortions, aberrations, and/or stray light. In some examples, transferring the light to sensor 40 includes imaging the sample region onto the sensor (e.g., onto a slit of the sensor, onto a sensing element of the sensor, and/or the like).

Light collected by collector 35 includes light emitted by, reflected by, and/or transmitted through objects within the sample region viewable by collector 35. The viewable region may be characterized by, e.g., an angular field of view (AFOV) and/or a horizontal or vertical field of view (FOV) of collector 35, e.g., at a desired working distance from the collector (e.g., at the object plane). The spectrum of the collected light (e.g., the intensity, brightness, radiance, and/or other level of the collected light as a function of wavelength) may be used to characterize objects within the sample region. For example, if the sample region includes a portion of a landmass, the collected light may primarily include light reflected from the landmass portion, and the spectrum of the reflected light may be used to infer mineral content of the landmass portion. The objects and/or portions of objects within the viewable sample region may be referred to as samples, and collecting light from the samples (e.g., acquiring a single spectrum and/or sequentially acquiring a plurality of spectra of the same viewable region) may be referred to as sampling.

Collector 35 may comprise any assembly of optical components suitable for collecting light from the sample region and transferring the collected light to sensor 40. For example, collector 35 may comprise an aperture, an entrance slit, an optical tube, and/or a fiber optic guide. An optical fiber configured to guide input light collected by an entrance aperture and/or fore-optic to the detector plane of sensor 40 may be useful when objects or other physical obscurations are disposed between the sample and the sensor, or when it is desirable to physically separate the sensor from the sample. For example, samples may be difficult to physically access due to space available or fragile environments such as in proximity to under-water vegetation, rock formations, or coral structures. In other cases, the optimal location of the optical sampling port on a deployment vessel, or reducing the instrument and vessel self-shading of the sample area, may require separating the instrument from the sampling entrance port.

Additionally, or alternatively, collector 35 may include a compound mirror and/or lens system with fore-optics; relay optics, diffusers, dispersive optical elements, and/or other homogenizing elements; polarizing elements; and/or adaptive telescope and/or microscope objectives with wavefront correction. In some examples, collector 35 includes optics configured to increase the uniformity of a spatial distribution (e.g., an angular distribution) of collected light. For example, collector 35 may include a diffusing collector with a cosine response, AKA a cosine corrector, configured to acquire a 180-degree FOV irradiance, and to accurately weight the angular distribution of an incoming incoherent light-field. A cosine corrector may be particularly useful for, e.g., measurements of sky irradiance or underwater downwelling or upwelling radiances. Light from an inhomogeneous source may also be generally made more uniform by a ground-glass diffuser, a fly's-eye homogenizer, or diffractive optical elements (DOE) within collector 35. In some examples, one or more linear polarizing optical elements and/or one or more circular polarizing optical elements are included in collector 35 to select and/or measure the polarization of the incoming light field as a function of wavelength and of angle of polarization. The angular orientation(s) of the polarizer(s) may be actuated manually and/or mechanically by automated and/or motorized control. The polarizing element or elements may be moved in or out of the optical path manually and/or mechanically by automated and/or motorized control. The polarizer(s) may be used, for example, to perform a hyperspectral polarization measurement to identify specific substances (e.g., substances having light-polarizing characteristics). A hyperspectral polarization measurement may be performed, for example, using light reflected from the surface of a body of water. Such light is typically polarized by the refraction and reflection at the air-water interface, and may be additionally polarized by the absorption from water molecules or other suspended matter in the surface layer. A circular polarizer may be used, for example, to reduce or amplify the light reflected from the surface of a body of water.

In some examples, collector 35 is configured to be dynamically actuated to vary the field of view, depth of focus, and/or other parameters. For example, collector 35 may include an entrance slit of adjustable size (e.g., an adjustable aperture, such as an iris). Optical diffusers, such as ground glass or quartz diffusers, may be used to mix the angular distribution of light across the sampled region. Additionally, or alternatively, positions of optical collector elements such as lenses may be adjustable. For example, optical collector elements may be mounted on translation stages such that distances between sensor 40 and optical collector elements is variable. In examples including adjustable collector elements, the size (e.g., spatial extent) of the pixels sampled by device 30 may be variable while the distance between sensor 40 and the sampled object is fixed. The spatial distribution sampled by device 30 may thus be varied without changing the position of sensor 40. Additionally, adjusting the position of the focal plane of a collector may help to sample the imaging contribution of a desired best-focus plane. Collector 35 may include steering optics configured to selectively change the lateral location of the image field and thereby scan a larger sampling area than possible with a fixed sampling location.

In some examples, optical elements within collector 35 may be individually adjustable and/or removable and replaceable. For example, optical collector elements may be mounted by bolts and/or screws to an optical breadboard having threaded bores. Additionally, or alternatively, collector 35 may be configured to be detachable from device 30 (e.g., from a housing of the device) and replaced with another collector. For example, a collector 35 configured to sample objects far away from device 30 may be replaced with a collector configured to sample objects very close to the device. The ability to adjust and/or replace collector 35 helps device 30 to collect data in a variety of settings and/or modes of deployment.

As described above, collector 35 is configured to transfer sampled light into sensor 40 (e.g., onto an entrance aperture of sensor 40). Sensor 40 may comprise any suitable device configured to receive light and to measure the level (e.g., an energy, power, and/or intensity) of the received light in a plurality of narrow spectral bands. Typically, sensor 40 includes a dispersive optical element configured to spatially separate spectral components of the received light, and one or more detectors configured to measure light intensity at a plurality of spatial points. The measured intensity at each spatial point corresponds to the intensity of light in a certain spectral band. The mapping between spatial points and spectral bands can be calculated based on, e.g., the dispersive properties of the dispersive element, the relative positions between the dispersive element and the spatial points, and so on. Sensor 40 is typically a compact optoelectronic device, such as a spectrometer or mini-spectrometer (see FIG. 3 and associated description in Section B). In some examples, however, sensor 40 may comprise another type of device, such as a spectrophotometer, a CCD array, a CMOS array, and/or the like.

Collector 35 may include optics configured to at least partially correct imperfections in the radiometric (spectral) or angular response of sensor 40 arising from wavefront aberrations introduced by various components of the sensor (e.g., an entrance aperture, a dispersive element such as grating or prism, coatings, and/or sensor imperfections). Sensor 40 may be disposed in any suitable position relative to collector 35 to receive the light from the collector. In some examples, sensor 40 may be positioned adjacent to and/or coupled to collector 35.

As shown in dashed lines in FIG. 2, device 30 optionally includes a second sensor 40, and may include a second collector 35 configured to collect light and transfer the collected light to the second sensor. In examples wherein device 30 includes two or more sensors, collectors corresponding to the two or more sensors may be configured to collect light incident from different directions. For example, the first collector may transfer light incident from a first direction onto the first sensor, and the second collector may transfer light incident from a second direction onto the second sensor. In some examples, a single collector 35 is configured to direct light from two different directions onto two different sensors. In examples wherein device 30 includes two or more collectors, the two or more collectors may have different optical properties (e.g., different fields of view, focal lengths, and/or the like), or may be substantially identical. If two or more sensors are included, they may have different properties (e.g., sensitivity, dynamic range, wavelength range, etc.) or may be substantially identical. Use of two or more sensors may enable device 30 to acquire data from two or more samples simultaneously. (However, see also Section D below, describing illustrative collectors configured to enable simultaneous measurements with a single sensor.) In addition to sensor 40, device 30 optionally includes one or more auxiliary sensors 50 such as GPS receivers, thermometers, pressure sensors (e.g., for depth and/or altimetry), humidity sensors, CTD sensors (AKA Sonde sensors), dissolved oxygen sensors, compasses, inertial measurement units, real-time clock (RTC) oscillators, photodiodes, pH sensors, dissolved Nitrogen (nitrates) sensors, dissolved organic carbon sensors, dissolved inorganic carbon sensors, and/or any other suitable sensors. The fusion of multiple sensor inputs may be very useful for precision optical measurements, because the output of one sensor (e.g., sensor 40 or one of auxiliary sensors 50) can be strongly coupled to a physical property measurable by a separate sensor. For example, the ability of sensor 40 to correctly measure the wavelength of light may depend linearly or nonlinearly on the temperature of the sensor and therefore on the temperature of the environment in which the sensor is used. Based on the relationship between measured wavelength and sensed temperature, a correction to the wavelength reading can be performed based on data measured by a temperature sensor in proximity to sensor 40. This improves the accuracy and stability of the obtained hyperspectral data. In some examples, corrections based on temperature (or other data measured by auxiliary sensor 50) are performed on board device 30 (e.g., by an electronics module) at the analog-circuit level and/or digitally (following the analog-to-digital conversion). Additionally, or alternatively, the correction may be implemented on an external computer after the data is transferred off-board the hyperspectral data-logging device.

Additionally, or alternatively, device 30 may include a light source 60. Light source 60 may be configured to illuminate at least a portion of the sampling region with a light having a predetermined intensity, propagation direction, polarization, and/or range of wavelengths. Light source 60 may enable measurements involving fluorescence, absorption, scattering, and/or the like.

Device 30 further includes an electronics module 70. Electronics module 70 includes a memory store 75 coupled to sensor 40 and configured to store data obtained by the sensor. Optionally, memory store 75 may be configured to store data from sensor 40 in association with data from auxiliary sensors 50 corresponding to, e.g., a timestamp corresponding to the time at which the data was collected, GPS coordinates, ambient temperature, settings of the sensor, and/or the like. Memory store 75 may be nonvolatile (e.g., configured to continue storing data when disconnected from a power source) and/or volatile (e.g., configured to discontinue storing data when disconnected from a power source). In examples including a volatile memory, using device 30 may include transferring data from the volatile memory to an external storage device prior to disconnecting the memory from a power source.

Electronics module 70 may include processing logic 78 configured to, e.g., trigger sensor 40 and/or auxiliary sensors 50 to start and/or stop collecting data, actuate adjustable elements of collector 35, write data from sensor 40 and/or auxiliary sensors 50 to memory store 75, and/or communicate with an input/output hub of device 30. For example, signals from auxiliary sensors 50 may be read by electronics module 70, which may selectively trigger sensor 40 to perform measurements based on the auxiliary sensor readings (e.g., when the auxiliary sensor readings satisfy one or more criteria). For example, electronics module 70 may trigger device 30 to perform measurements in response to signals from a pressure sensor indicating that the device (or portion thereof, such as collector 35) is disposed at a predetermined depth underwater. As another example, electronics module 70 may trigger sensor 40 to perform measurements in response to signals from a tilt sensor (e.g., an IMU) indicating a predetermined orientation of collector 35 or other components of the device. The predetermined orientation may, for example, enable measurements of sky radiance at a desired angle relative to the horizon and/or to the sun. As yet another example, signals from a clock or a GPS receiver may be used to trigger measurements at desired times and/or locations.

In some examples, two or more criteria are associated with the information sensed by a single auxiliary sensor. For example, electronics module 70 may perform an action (e.g., trigger a reading, vary a sampling rate and/or integration time of sensor 40, etc.) based both on the actual value of data acquired by the auxiliary sensor and on the rate at which the data changes with time. For example, if information sensed by a depth sensor indicates that the depth of device 30 below water is at least a predetermined amount and is also changing rapidly, electronics module 70 may increase the rate at which the system acquires data.

In some examples, auxiliary sensors 50 include at least one photodiode (or other suitable device), and electronics module 70 is configured to turn off power to sensor 40, at least some auxiliary sensors 50, and/or other components of device 30 in response to data from the photodiode indicating that light levels are below a predetermined threshold. The predetermined threshold may correspond to light levels associated with a time of day (e.g., night-time), with a specified depth underwater, and/or with a specified tilt angle. Electronics module 70 may restore power in response to information from the photodiode indicating that light levels are above the predetermined threshold. Shutting down power based on information sensed by the photodiode may reduce total power consumption of device 30 during deployment, and may thereby extend the length of deployment of an autonomous and/or manually operated device.

Additionally, or alternatively, electronics module 70 may power down components of device 30 in response to information from a real-time clock. For example, electronics module 70 may shut down sensor 40 and auxiliary sensors 50 when the real-time clock indicates that it is night time, and may turn on power to sensor 40 and auxiliary sensors 50 when the real-time clock indicates that it is morning.

In some examples, triggering may be additionally or alternatively based on signals from sensor 40. For example, electronics module 70 may vary the sampling rate or integration time of sensor 40 based on the intensity of light recently measured by the sensor (e.g., across the entire spectrum measurable by sensor 40 or across any suitable portion(s) of the measurable spectrum). In this way, device 30 may autonomously adapt to, e.g., changing amounts of incident light. For example, electronics module 70 may change settings of sensor 40 to settings suitable for low amounts of light when the measured intensity is low, and, in response to an increase in measured intensity, change the settings to be suitable for larger amounts of light.

Device 30 further includes an input/output hub 80 allowing for communication of data between device 30 and other devices (e.g., computers, mobile devices, servers, and/or the like). For example, input/output hub 80 may include one or more interface ports such as serial ports, parallel ports, and/or universal serial bus (USB) ports. The interface ports may include dedicated input ports, dedicated output ports, and/or ports capable of both input and output. For example, a USB port may be used to provide input to device 30 and to output information from the sensing system to an external computer or other external device. In some examples, input/output hub 80 includes a wireless communication circuit, which may transmit and/or receive information using, e.g., a WiFi wireless technology protocol, a Bluetooth® wireless technology protocol, an Iridium® wireless communications system, and/or the like. Input/output hub 80 may be used to retrieve data from device 30 (e.g., from memory store 75, from a buffer within electronics module 70, and/or directly from sensor 40). For example, data may be transferred via input/output hub 80 to an external computer for storage and/or analysis. Input/output hub 80 may additionally or alternatively be used to input instructions related to the operation of device 30. For example, a user may use an external computer and/or mobile device coupled to input/output hub 80 to select a parameter of sensor 40 (e.g., integration time, sampling rate, and/or the like). The selected parameter is communicated via input/output hub 80 to sensor 40 and/or to electronics module 70.

In some examples, device 30 includes one or more data processing systems (e.g., computers), such as a single-board Linux computer and/or other suitable system. The data processing system may communicate with, and/or be part of, electronics module 70 and/or input/output hub 80. The data processing system may facilitate transfer of data between device 30 and an external system. In some examples, the data processing system remains in a low-power standby mode until woken by electronics module 70 (e.g., by one or more microcontrollers of the electronics module) for data transfer and/or any other suitable purpose. In this manner, power is conserved by keeping the computer in standby mode during much of the time the device is deployed.

Device 30 further includes a power source 90. Power source 90 may include any suitable battery or batteries, rechargeable or otherwise, such as a lead-acid battery, a lithium-ion battery, a lithium-polymer battery, a nickel-cadmium battery, and/or the like. The battery may be a secondary cell in communication with a battery-charging circuit configured to receive power from an external source and convert the received power into an electrical current usable to charge the battery (e.g., a DC current). The charging circuit may be configured to charge the battery by inductive charging, infrared power transmission, radio-frequency power transmission, and/or by drawing power from another device via a USB interface port. Power source 90 provides power to components of device 30 having need of a power supply (e.g., needing a voltage or current source). For example, power source 90 may supply electrical power to sensor 40, any motorized components of collector 35, input/output hub 80, electronics module 70, light source 60, and/or auxiliary sensors 50. In some examples, power source 90 comprises a photovoltaic device (e.g., one or more photovoltaic panels, and/or any other suitable solar power device).

Typically, device 30 includes an enclosure or housing 95 configured to at least partially contain the components described above. Housing 95 is generally designed to be suitable for deployment in rough environments (e.g., outdoors, on ships and/or buoys, on aerial vehicles, etc.). For example, the housing may be water-resistant or water-tight, and may be configured to resist corrosion. In some examples, housing 95 is configured to protect its contents when deployed underwater.

B. Illustrative Compact Spectrometer

Figure 3:
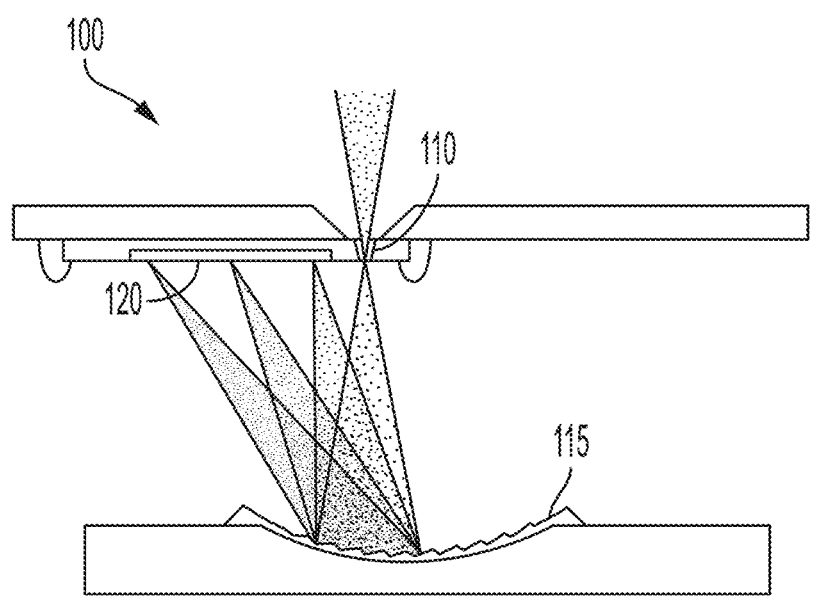
FIG. 3 is a is a schematic diagram of an illustrative compact spectrometer in accordance with aspects of the present teachings.

With reference to FIG. 3, this section describes an illustrative compact spectrometer 100. Compact spectrometer 100 is an example of sensor 40 suitable for use in a hyperspectral sensing system in accordance with aspects of the present teachings, as described above. Accordingly, compact spectrometer 100 is configured to measure an intensity of impinging light in each of a plurality of adjacent narrow spectral bands. Compact spectrometer 100 may be referred to as a microspectrometer, and/or an ultra-compact spectrometer.

FIG. 3 is a schematic depiction of compact spectrometer 100. As shown in FIG. 3, compact spectrometer 100 includes an input slit 110 through which incident light enters. The incident light is typically light emitted by, reflected by, scattered from, and/or transmitted through sample objects within the field of view of collector 35. Collector 35 directs the incident light through input slit 110, which may include imaging the sample objects onto input slit 110.

The incident light is transmitted through a hollow space in compact spectrometer 100 and impinges on grating 115. Grating 115 is a diffraction grating comprising an array of fine, parallel grooves on a curved reflective substrate. In the example depicted in FIG. 3, grating 115 comprises a reflective concave blazed grating, having grooves shaped to form right triangles, but any suitable type of grating may be used (e.g., a holographic grating, a ruled grating, an echelle grating, and/or any other suitable grating). In some examples, a different dispersive element (e.g., a transmissive grating and/or a prism) is used instead of grating 115.

In general, light impinging on grating 115 is reflected from the grating in a propagation direction determined at least partially by the wavelength of the light. In other words, grating 115 disperses or separates the incident light into a plurality of chromatic components (e.g., spectral component or colors), and the chromatic components are reflected from the grating in a wavelength-dependent manner.

The curvature of grating 115, which is concave toward input slit 110, focuses the reflected incident light toward an image sensor 120. Image sensor 120 is configured to measure an amount (e.g., an intensity) of the dispersed and reflected incident light from grating 115 at each of a plurality of spatial positions and/or pixels of the image sensor. Because grating 115 reflects light in a wavelength-dependent direction, the location on image sensor 120 at which light was measured corresponds to the wavelength of the light. Image sensor 120 may comprise a linear CMOS array (e.g., a CMOS device comprising a row of detecting pixels), a CCD array, and/or any other suitable image-sensing device. In some examples, grating 115 and/or image sensor 120 comprise optoelectronic chips.

Compact spectrometer 100 has a high sensitivity to light, enabling it to acquire hyperspectral data in low-light environments, such as underwater. Compact spectrometer 100 also has a relatively short electro-optical integration time (e.g., it can complete a measurement in a short amount of time). As a result of its high sensitivity and short integration time, compact spectrometer 100 has a wide dynamic range. In other words, it is capable of measuring both low levels and high levels of light. The wide dynamic range of compact spectrometer 100 enables device 30 to be used in dark underwater environments as well as bright above-water environments.

Due to its small size, compact spectrometer 100 has a short optical path length. That is, light travels a relatively small distance within compact spectrometer 100. The short optical path length allows for high stability against vibrations, thermal changes, optical defects, stray light, and/or other disruptions.

Suitable examples of compact spectrometer 100 include the compact spectrometer currently sold under the name "C12880MA" by Hamamatsu Photonics and the Carl Zeiss Spectroscopy GmbH product named "Monolithic Miniature Spectrometer, MMS UV-VIS". Other suitable examples of compact spectrometer 100 may include a spectrometer that supports a spectral response up to 850 nm or more (e.g., a spectral domain of 300 nm to 900 nm, of 330 nm to 850 nm, and/or any other suitable range), has a maximum spectral resolution of 15 nm, is sized approximately 20×13×10 mm, and/or weighs approximately 5 grams or less. Larger size sensor modules or packages with sizes approximately 70×60×40 mm and weighing 50 grams or less may be suitable also.

C. Illustrative Devices Having a Light Source

Figure 4:
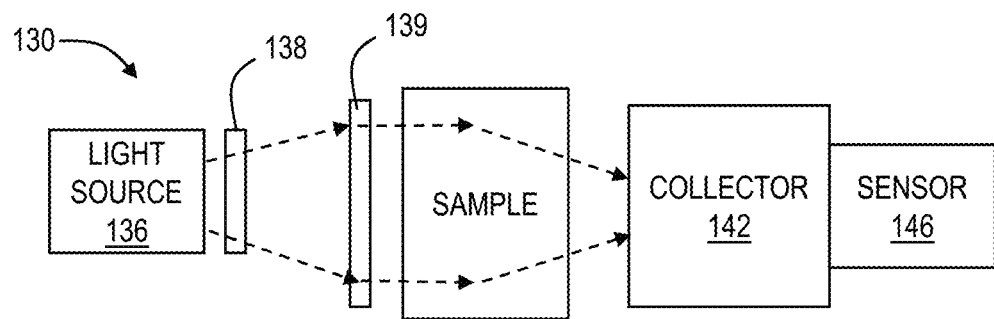
FIG. 4 is a schematic diagram depicting a hyperspectral sensing system performing a measurement on a discrete sample, in accordance with aspects of the present teachings.
Figure 5:
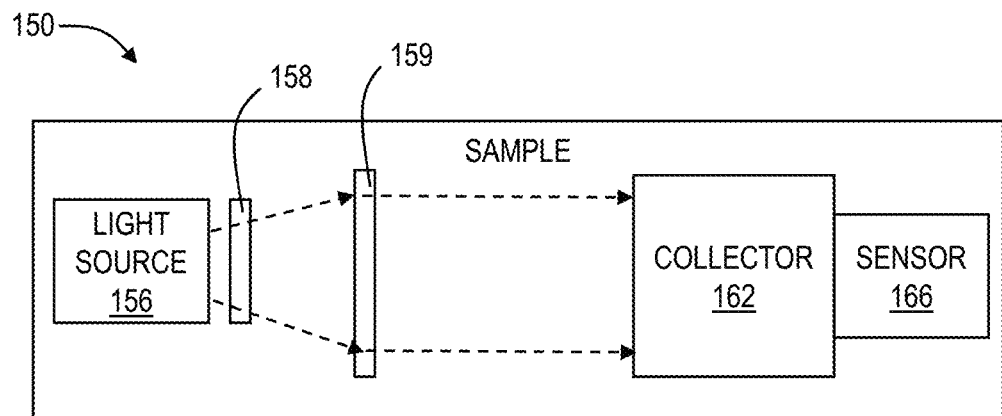
FIG. 5 is a schematic diagram depicting a hyperspectral sensing system performing a measurement while immersed in a water sample, in accordance with aspects of the present teachings.
Figure 6:
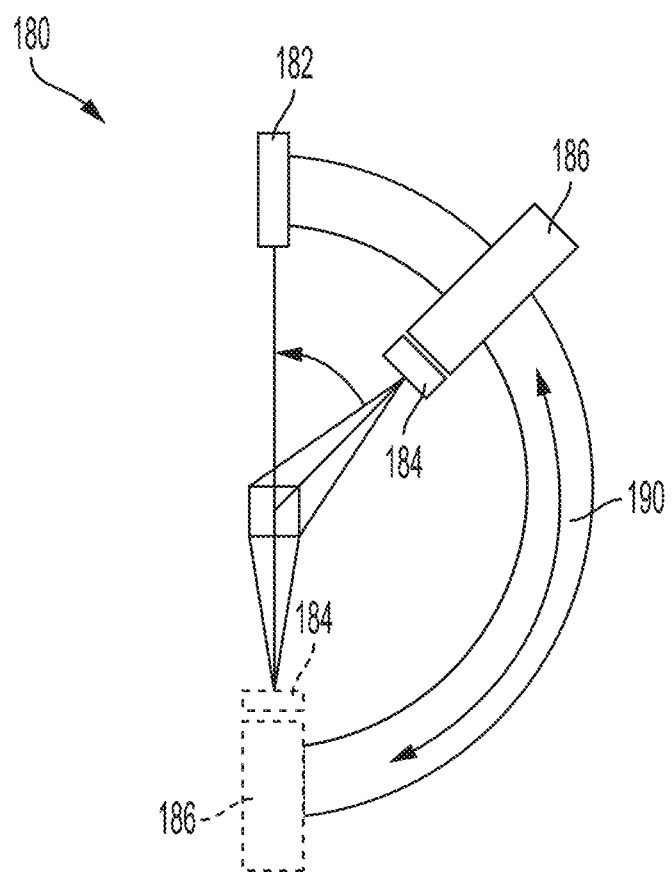
FIG. 6 is an illustrative hyperspectral sensing device configured for performing angularly-resolved hyperspectral measurements, according to aspects of the present teachings.
Figure 7:
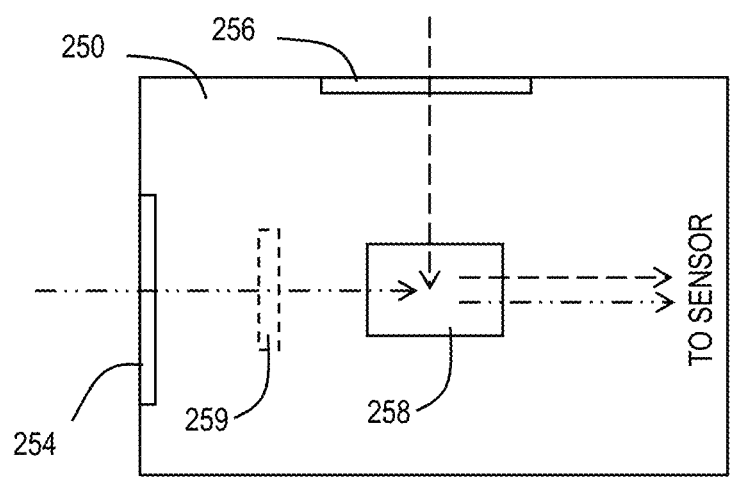
FIG. 7 is a schematic diagram of an illustrative optical collector configured to simultaneously collect radiance from two different directions in accordance with aspects of the present teachings.
Figure 8:
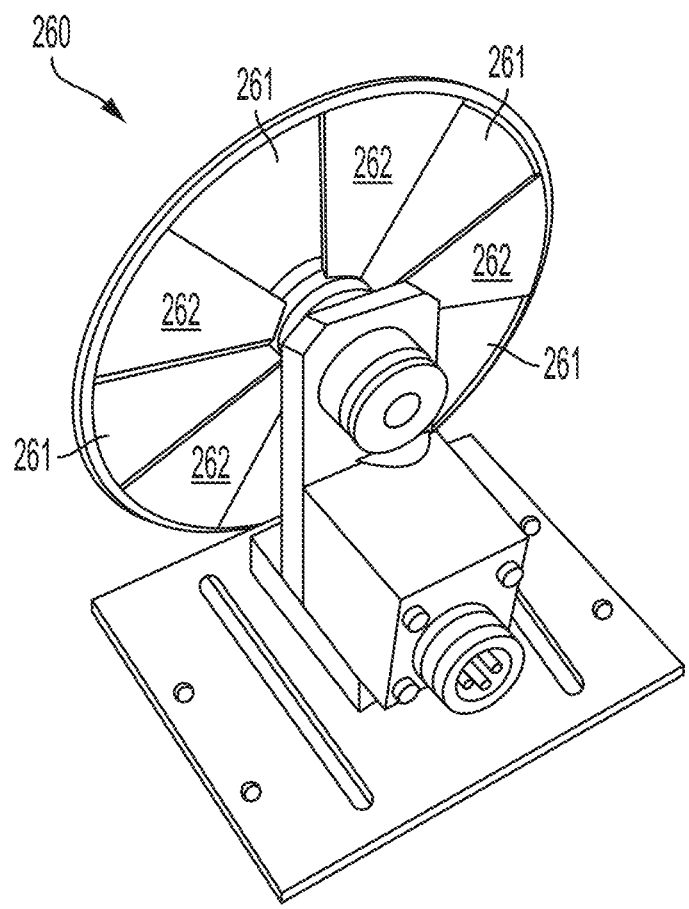
FIG. 8 is an isometric view of an illustrative chopper wheel configured to modulate light according to aspects of the present teachings.

As shown in FIGS. 4-6, this section describes illustrative hyperspectral sensing devices including light sources (e.g., LEDs, lamps, and/or lasers) and configured to illuminate a sample so that scattering, fluorescence, and/or absorption properties of the sample may be probed. These devices may be substantially similar to device 30 in at least some respects. The sample may be, e.g., a sample of air or a sample of water. In some embodiments, the sample is a defined volume of gas, liquid, or solid matter inside a container.

FIG. 4 schematically depicts a device 130 configured to illuminate a discrete and/or flow-through sample. For example, the sample may be a discrete sample removed from the sampling site (such as a defined quantity of water removed from a body of water using, e.g., a profiling rosette, bottle, and/or other suitable device). Alternatively, or additionally, the sample may be a flow-through sample configured to be passed through the viewable region of the sensing system (for example, water may be pumped from a body of water through a sampling chamber disposed in front of the optical collector, so that a measurement or series of measurements of the flowing water may be made).

Device 130 includes a light source 136, which comprises one or more devices configured to emit light, such as LEDs, OLEDs, diode lasers, fiber lasers, lamps, and/or the like. In some examples, the one or more light-emitting devices of light source 136 each produce light substantially at a single wavelength. For example, LEDs producing light at 405 nm, 470 nm, 560 nm, and/or 650 nm may be used. In some examples, one or more of the light-emitting devices produce light at a range of wavelengths. For example, light source 136 may include broadband LEDs (e.g., superluminescent LEDs), a continuum and/or supercontinuum source, and so on. The wavelength range of light source 136 may be selected based on specific absorbing, scattering, and/or fluorescing substances expected to be present in the sample. Light source 136 may be modulated (e.g., amplitude-modulated and/or phase-modulated) such that light from the light source may be distinguished and/or isolated from background and/or ambient light (with or without lock-in amplification).

Device 130 includes an optical assembly configured to prepare light produced by the source for transmission to the sample. Typically, the optical assembly includes a diffuser 138 configured to homogenize (e.g., diffuse) light produced by the light source, and a lens 139 configured to collimate light produced by the light source (e.g., to telecentrically illuminate the sample). These components preserve the focal plane of the light source across the sample volume.

In some examples, light source 136 and/or the associated optical assembly may be mounted detachably to device 130 so that they can be removed when not needed, or swapped out for different components.

Device 130 includes an optical collector 142 configured to collect light from the sample and to transfer it to a sensor 146 (e.g., a compact spectrometer or other suitable detector having sufficient spectral resolution for hyperspectral measurements). Collector 142 may include one or more bandpass and/or notch optical filters configured to block light produced by light source 136 that is transmitted through the sample, or passes around the sample, substantially without interacting with the sample. These filters may, for example, increase a signal-to-noise ratio of the hyperspectral measurement, and/or may prevent a weak fluorescence signal received at sensor 146 from being overwhelmed by a strong background signal from light source 136.

In some examples, one or more optical components of collector 142 are selected based on optical properties associated with a bottle or other device containing the sample (e.g., based on an amount of refraction experienced by light passing through the bottle). Device 130 may be configured to be used with any one of a plurality of interchangeable collectors having different optical components.

FIG. 5 schematically depicts an illustrative device 150 configured to acquire hyperspectral data using a light source while immersed in a sample. For example, device 150 may be immersed in water, may be used to measure ambient air, and/or may be used in any other situation wherein the entire optical path between the light source and the optical collector is occupied by the sample. Device 150 includes a light source 156, a light-source diffuser 158, a light-source collimating lens 159, an optical collector 162, and a sensor 166.

FIG. 6 schematically depicts an illustrative device 180 configured for selectively adjusting an angle formed by a light source 182 relative to a collector 184 and a sensor 186. Collector 184 and sensor 186 are mounted slidably on a rail 190, as shown in FIG. 6. Typically, collector 184 and sensor 186 are connected rigidly, such that they move together along the rail, but other configurations are possible. In a first position, the collector and sensor are disposed such that light from light source 182 passes through a sample, and light transmitted directly through the sample (e.g., without deflection) enters the collector. In the first position, collector 184 and sensor 186 face light source 182 (e.g., forming a substantially 180-degree angle with the light source) with the sample disposed between them.

With collector 184 and sensor 186 in the first position, the spectral properties of light striking the sensor can be measured and compared with known spectral properties of light source 182, and absorbance properties of the sample may be inferred. For example, a measurement indicating that the sample preferentially absorbs light at a certain wavelength may indicate that the sample contains a substance known to absorb light at that wavelength. This type of measurement may be referred to as an attenuation measurement, because the wavelength-dependence of the attenuation of light within the sample is probed.

In a second position, collector 184 and sensor 186 are disposed at an angle less than 180° relative to light source 182. In some cases, the angle may be less than 90°. In the second position, device 180 may measure spectral properties of light scattered from the sample. For example, sensor 186 may detect light produced by photons from light source 182 undergoing Rayleigh scattering, Raman scattering, Brillouin scattering, and/or diffuse reflection from the sample. Additionally, or alternatively, sensor 186 may detect light produced by photons from light source 182 inducing fluorescence in the sample, and/or in a constituent of the sample. The spectrum of light detected at one or more selected angles may be used to determine concentrations of specific substances within the sample (e.g., concentrations of algae within water). In some examples, hyperspectral measurements of fluorescence may indicate the size of particulates within the sample, a concentration of a specific substance within the sample, a type of substance present in the sample, and/or a physiological state of a biological species within the sample.

Collector 184 and/or sensor 186 may transition between the first and second positions by sliding along rail 190. Additional positions along rail 190 may be possible, e.g., at angles between 0° and 180° relative to light source 182. In some examples, the variation of the sample spectrum in response to changes in the angle subtended by the collector optical axis and the angle of the excitation source may be probed. The angular dependence of the spectrum may indicate Rayleigh scattering in the sample and therefore may be used to detect a presence or abundance of small particles (e.g., particles <0.5 microns in size).

In some examples, collector 184 and sensor 186 are moved by an actuator, and rail 190 is a fixed armature of the actuator. The actuator may enable the collector and sensor to be positioned with high accuracy and precision for reproducible angularly-resolved measurements. In some examples, light source 182 slides along the rail while collector 184 and sensor 186 are fixed in place.

D. Illustrative Collectors for Simultaneous Measurement

With reference to FIGS. 7-14, this section describes illustrative optical collectors for use in simultaneous hyperspectral measurements of light propagating from two different directions using a single sensor (e.g., a single spectrometer). In some examples, light from one direction is propagating from the sky, and light from the other direction is propagating from a body of water. Simultaneous sky-water measurements may, for example, be used to determine spectral properties of a body of water such as an ocean, coastal region, lake, reservoir, estuary, river, and/or the like. For convenience, collectors configured for use in measurement of light from two directions are described herein in the context of simultaneous sky and water radiance measurements. However, generally, light from the two directions may have any suitable origin.

In some examples, a body of water may be characterized by a spectral remote-sensing reflectance, e.g., a wavelength-dependent ratio of radiance leaving the water in a particular viewing direction to the total sky irradiance just above the water's surface. The remote-sensing reflectance $R_{rs}$ may be defined by the following equation:

$$R_{rs}(\theta, \varphi, \lambda) = \frac{L_w(\theta, \varphi, \lambda)}{E_d(\lambda)}$$

where $L_w(\theta,\varphi,\lambda)$ is the radiance of water-leaving light at wavelength $\lambda$ in a direction defined by polar and azimuthal angles $(\theta,\varphi)$ and $E_d(\lambda)$ is the irradiance of downwelling light at wavelength A incident on the water surface. Downwelling light typically includes light from the sky. Water-leaving light includes light emerging from beneath the surface of the water, such as light from the sky that traveled beneath the surface and was scattered upward through the surface. Water-leaving light by definition does not include light reflected directly from the surface of the water substantially without traveling underwater. In general, a direct measurement of the water-leaving radiance is not possible because a detector pointed at the water surface will measure the total upwelling radiance, which includes both the water-leaving radiance and the surface-reflected radiance. That is, a detector measures $$L_T(\theta,\varphi,\lambda)=L_w(\theta,\varphi,\lambda)+L_r(\theta,\varphi,\lambda)$$

where $L_T(\theta,\varphi,\lambda)$ is the total upwelling radiance and $L_r(\theta,\varphi,\lambda)$ is the surface-reflected radiance. The water-leaving radiance may, however, be estimated from the total upwelling radiance by several methods. In some methods, the surface-reflected radiance is estimated by multiplying the sky radiance by a correction factor. For example, $$L_r(\theta,\varphi,\lambda)=\rho L_s(\theta',\varphi',\lambda)$$

where the angles $(\theta',\varphi')$ denote a direction within the field of view of the detector when the detector is pointed in a direction suitable for sampling the sky radiance that would specularly reflect from the water surface into the direction defined by $(\theta,\varphi)$. The correction factor $\rho$, which may be a Mobley surface correction, may depend on either or both angles $(\theta,\varphi)$, wavelength $\lambda$, and/or other factors such as environmental factors. Using this estimate for the surface-reflected radiance, the remote-sensing reflectance may be estimated as $$R_{rs}(\theta, \varphi, \lambda) = \frac{L_T(\theta, \varphi, \lambda) - \rho L_s(\theta', \varphi', \lambda)}{E_d(\lambda)}.$$

In other examples, the surface correction of the sky radiance can be explicitly modeled using a bidirectional reflectance distribution function (BRDF) using the known imaging view geometry (e.g., solar zenith and azimuth angles, and sensor zenith and azimuth view angles), a model of the angle and/or wavelength-dependent reflectance at the air-water interface, and the interface roughness due to wave facets on the water surface. Alternatively, or additionally, a plurality of sensors may measure the total upwelling radiance from different angles, and the surface correction may be obtained based on the measurements. In these examples, measuring the sky radiance is optional.

The downwelling irradiance $E_d(\lambda)$ may be estimated by measuring the reflectance of a reference surface having a known reflectance parameter $R_{ref}$. A typical reference surface is a flat, rigid plaque configured to reflect incident light diffusely and isotropically (e.g., a Lambertian reflector). For example, a card coated with barium sulfate and/or magnesium oxide may be used as a plaque. The radiance $L_{ref}$ of light reflected by the plaque is independent of the measurement angle and may be calculated as $$L_{ref}(\lambda) = \left(\frac{R_{ref}(\lambda)}{\pi}\right) E_d(\lambda).$$

The remote-sensing reflectance for a given wavelength in a given direction may then be calculated from the measured total upwelling radiance, the measured sky radiance, and the measured reference plaque reference:

$$R_{rs} = \frac{(L_T - \rho L_s)}{\pi(L_{ref}/R_{ref})}.$$

In other examples, the downwelling irradiance may be measured directly.

In known systems for remote-sensing radiance measurements, the sky radiance and the total upwelling radiance are typically measured in sequence with a single detector or simultaneously with multiple respective detectors. (The reference plaque, if used, may be measured at the same time as the total upwelling radiance, or may be measured independently.) Both sequential measurements and multiple-detector measurements have disadvantages. Environmental conditions may change significantly between sequential measurements, leading to uncertainty and/or noise in the measured data. Data acquired by multiple detectors may include errors due to the detectors having different sensitivities, being imperfectly calibrated, and/or triggering data acquisition at slightly different times. Systems and methods of the present disclosure allow simultaneous measurement of the total upwelling radiance, sky radiance, and optionally a reference plaque radiance, using a single hyperspectral-capable sensor (e.g., a single compact spectrometer).

Illustrative sky-water collectors configured to collect light for a simultaneous sky-water measurement are described below. As defined herein, a simultaneous sky-water measurement is a substantially simultaneous measurement of total upwelling radiance and sky radiance, and may include a substantially simultaneous or a non-simultaneous measurement of a reference plaque. An illustrative sky-water collector 250 is depicted schematically in FIG. 7. Sky-water collector 250 includes a sky-radiance aperture 254 configured to allow light to enter the collector, a water-radiance aperture 256 configured to allow light to enter the collector, and an optical director 258 (e.g., an assembly of optical components) configured to direct light entering through the sky-radiance aperture and light entering through the water-radiance aperture toward a sensor within the device. Sky-radiance aperture 254 and water-radiance aperture 256 may include slits of fixed or variable width, optical diffusers, lenses, and/or other optical components. Optionally, sky-water collector 250 may include steering optics (e.g., mirrors, filters, polarizers, polarizing and/or nonpolarizing beamsplitters, and/or other steering components) configured to direct light in one or more directions, refractive and/or diffractive elements configured to adjust beam sizes and/or shapes of light, beam blocks configured to block light from entering one or more portions of the collector, and/or modulators configured to modulate light (e.g., to modulate a phase and/or amplitude of light).

Optionally, a modulator 259 may be disposed between sky-radiance aperture 254 and optical director 258 and configured to modulate light entering through sky-radiance aperture 254, such that the portions of light entering the collector through that aperture may be distinguished. Additionally, or alternatively, a modulator may be disposed between water-radiance aperture 256 and optical director 258.

Modulator 259 may comprise any suitable system or device configured to modulate light. In some examples, modulator 259 includes a scanning optical element configured to periodically deflect light such that at least a portion of the light deviates from the optical path it would otherwise travel. For example, a scanning mirror may periodically deflect the light such that the light is not directed toward a sensor, or such that the light strikes a beam block within sky-water collector 250.

Additionally, or alternatively, modulator 259 may comprise a chopper wheel 260. Chopper wheel 260, depicted in FIG. 8, includes an opaque substrate (e.g., a disc) having openings 261 at regular angular intervals. Adjacent openings 261 are separated by unmodified blocking portions 262 of the opaque substrate. Chopper wheel 260 is rotatably mounted to a support and configured to rotate at a fixed, stable rate (e.g., a motor may drive the chopper wheel to rotate at a specific speed). Light may be amplitude-modulated by placing chopper wheel 260 in the optical path of the light. As chopper wheel 260 rotates, the light is periodically blocked by blocking portions 262 and allowed to pass by intervening openings 261. The periodic blocking effectively modulates the amplitude of the light.

In examples including modulation of light entering through one or more apertures, an electronics module (e.g., electronics module 70) may be configured to trigger data acquisition by the sensor in phase (and frequency) with the modulation cycle of the modulator. For example, data acquisition may be triggered in phase with the blocking of the incoming light by chopper wheel 260, or in phase with the passing of the light through openings 261 of chopper wheel 260. In this way, data acquired by the sensor when one or more apertures are blocked by chopper wheel 260 may be compared with data acquired when no apertures are blocked by chopper wheel 260, and so the contribution of light from each aperture may be identified. In some examples, a lock-in amplifier is used to selectively amplify the modulated signal and reject any signals that do not vary with the phase and/or frequency associated with the modulator.

Although sky-water collectors disclosed herein are primarily described as enabling measurement of light from sky and from water simultaneously, they may be used to simultaneously measure light from any two suitable sources. For example, a sky-water collector may be included in a hyperspectral sensing device deployed underwater, and the sky-water collector may collect light originating near the floor of the body of water and light originating near the surface of the body of water. The hyperspectral sensing device may then simultaneously measure radiances of floor light and surface light.

Illustrative examples of sky-water collectors are described below. Various components of the illustrative sky-water collectors described below may be combined in any suitable combination.

i. Illustrative Convex Reflector Collector

Figure 9:
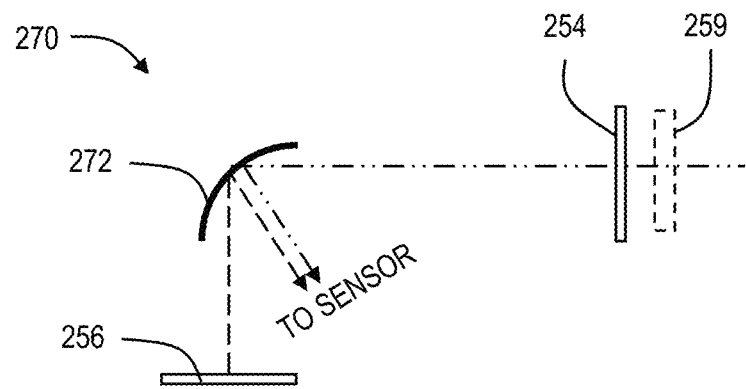
FIG. 9 is a schematic diagram of an illustrative optical collector including a convex reflector, in accordance with aspects of the present teachings.

An illustrative convex reflector collector 270 is depicted in FIG. 9. Convex reflector collector 270 is an example of sky-water collector 250. Convex reflector collector 270 includes a convex reflector 272, which is an example of optical director 258. Convex reflector 272 is a curved reflective element configured to direct light entering convex reflector collector 270 toward the sensor. Convex reflector 272 may focus light at a primary focus point between the convex reflector and the sensor. Sky-radiance aperture 254, water-radiance aperture 256, and convex reflector 272 are disposed such that light entering through the water-radiance aperture and light entering through the sky-radiance aperture reflect from the convex reflector along substantially parallel optical paths and/or substantially overlapping optical paths (e.g., light from the two apertures may co-propagate after reflecting from the convex reflector). Modulator 259 may be disposed adjacent one of the apertures such that light entering the aperture is modulated prior to reflecting from convex reflector 272. In the example depicted in FIG. 9, modulator 259 is disposed exterior to sky-radiance aperture 254, but modulators may additionally or alternatively be disposed interior to the sky-radiance aperture, and/or exterior and/or interior to water-radiance aperture 256. For example, modulator 259 may be disposed interior to the sky-radiance aperture, such that modulator 259 is disposed between the sky-radiance aperture and convex reflector 272.

ii. Illustrative Movable Reflector Collector

Figure 10:
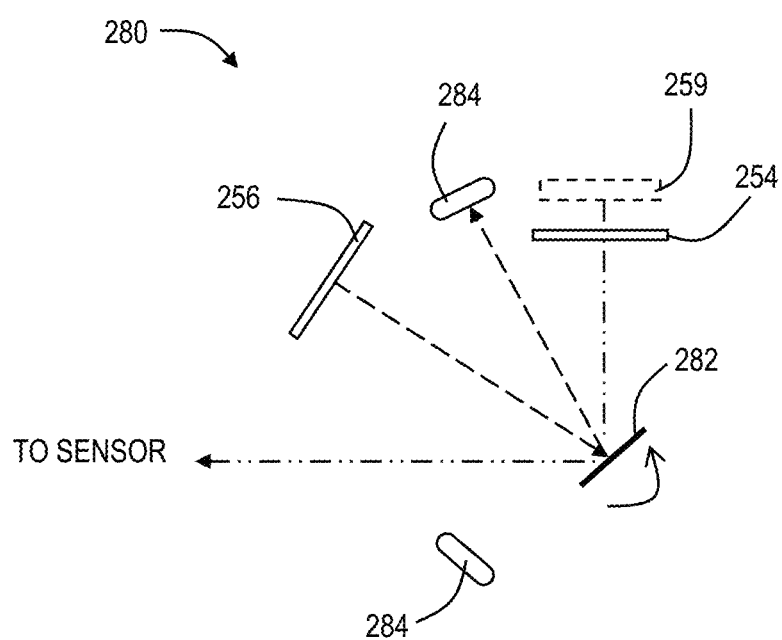
FIG. 10 is a schematic diagram of an illustrative optical collector including a movable reflector, in accordance with aspects of the present teachings.

An illustrative movable reflector collector 280 is depicted in FIG. 10. Movable reflector collector 280 is an example of sky-water collector 250. Movable reflector collector 280 includes a movable reflector 282, which is an example of optical director 258. Movable reflector 282 comprises a reflective optical element mounted rotatably within movable reflector collector 280. Movable reflector 282 may additionally or alternatively be mounted translatably within movable reflector collector 280. Movable reflector 282, sky-radiance aperture 254, and water-radiance aperture 256 are disposed within movable reflector collector 280 such that positioning the movable reflector at a first position (e.g., a first orientation) causes light entering from the sky-radiance aperture to be reflected toward sensor 40 and light entering from the water-radiance aperture to be reflected away from the sensor, and positioning the movable reflector at a second position causes light entering from the sky-radiance aperture to be reflected away from the sensor and light entering from the water-radiance aperture to be reflected toward the sensor. The position of movable reflector 282 may be adjusted very quickly to switch between measurements of sky radiance and water radiance, and no other component of movable reflector collector 280 requires adjustment to switch from sky to water radiance measurements. Therefore, movable reflector collector 280 may be described as capable of substantially simultaneous measurements of sky and water radiance.

One or more beam blocks 284 configured to substantially prevent transmission and specular reflection of impinging light may be disposed within movable reflector collector 280 to block light that is not directed toward the sensor. Use of beam blocks 284 may reduce stray light reaching the sensor and thereby decrease noise and uncertainty in the hyperspectral measurement. Movable reflector collector 280 may include one or more modulators 259.

iii. Illustrative Movable Disperser Collector

Figure 11:
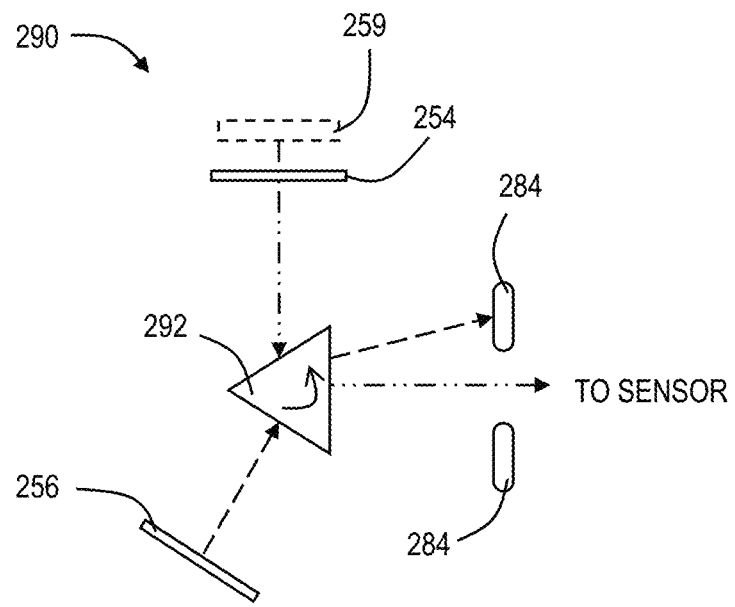
FIG. 11 is a schematic diagram of an illustrative optical collector including a movable dispersing element, in accordance with aspects of the present teachings.

An illustrative movable disperser collector 290 is depicted in FIG. 11. Movable disperser collector 290 is an example of sky-water collector 250. Movable disperser collector 290 includes a movable dispersing element 292, which is an example of optical director 258. Movable dispersing element 292 is a dispersing optical element (e.g., a prism, grating, and/or any other suitable element configured to direct light in a wavelength-dependent direction) mounted rotatably within movable disperser collector 290, and may additionally or alternatively be mounted translatably within the collector.

Movable dispersing element 292, sky-radiance aperture 254, and water-radiance aperture 256 are disposed within movable disperser collector 290 such that positioning the movable dispersing element at a first position (e.g., a first orientation) causes light entering from the sky-radiance aperture to be reflected toward the sensor and light entering from the water-radiance aperture to be reflected away from the sensor, and positioning the movable dispersing element at a second position causes light entering from the sky-radiance aperture to be reflected away from the sensor and light entering from the water-radiance aperture to be reflected toward the sensor. Beam blocks 284 may be disposed within movable disperser collector 290 to block stray light from the detector. Modulator 259 may be included. Because movable dispersing element 292 spatially separates light according to wavelength, dispersing elements typically included in the sensor may be omitted when movable disperser collector 290 is used. For example, the sensor may comprise replaced by a linear CMOS or CCD array rather than a spectrometer.

iv. Illustrative Beamsplitter Collector

Figure 12:
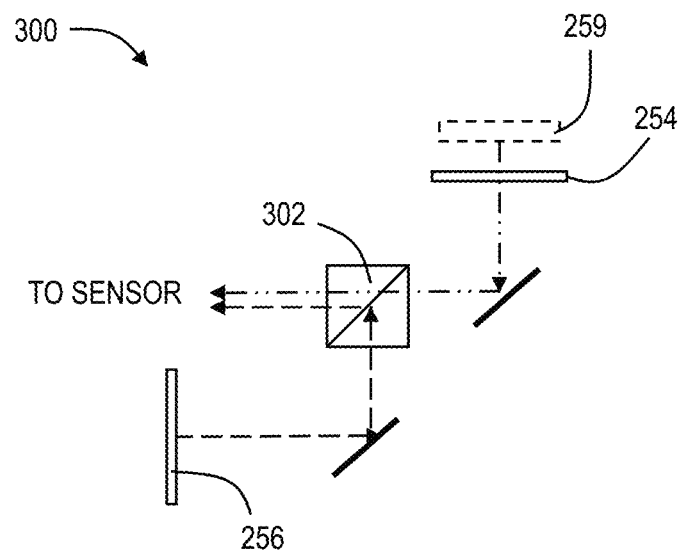
FIG. 12 is a schematic diagram of an illustrative optical collector including a beamsplitter, in accordance with aspects of the present teachings.

An illustrative beamsplitter collector 300 is depicted in FIG. 12. Beamsplitter collector 300 is an example of sky-water collector 250. Beamsplitter collector 300 includes a beamsplitter 302 configured to combine light impinging on the beamsplitter from two or more directions into a single copropagating beam of light. Typically, beamsplitter 302 is configured to reflect a portion of incoming light and to transmit a portion of incoming light. Beamsplitter 302 may comprise a partially reflecting mirror, a beamsplitter cube, a fiber-optic beamsplitter, a half-silvered mirror, a pellicle (e.g., a thin membrane), a waveguide beamsplitter, and/or a micro-optic beam splitter. Beamsplitter 302, sky-radiance aperture 254, and water-radiance aperture 256 are disposed within beamsplitter collector 300 such that light from the sky-radiance aperture and light from the water-radiance aperture impinge on the beamsplitter from different directions and are emitted by the beamsplitter in the same direction toward the sensor. One or more transmissive polarizing elements (e.g. a wire-grid polarizer, a quarter-wave plate, etc.) and/or reflective polarizing elements (e.g., a thin film, another beamsplitter, etc.) may be disposed between beamsplitter 302 and sky-radiance aperture 254, and/or between beamsplitter 302 and water-radiance aperture 256, in order to polarize the light. The polarizing elements may polarize the light linearly, circularly, and/or elliptically. Beamsplitter 302 may be a polarizing beamsplitter, and the polarizing elements may be configured to polarize the sky light and/or water light such that substantially all of the sky light and water light is combined at the beamsplitter and directed toward the sensor. Additionally, beam blocks, mirrors and/or other suitable reflectors, and/or modulators may be included as needed.

v. Illustrative Sky-Water-Plaque Collector

Figure 13:
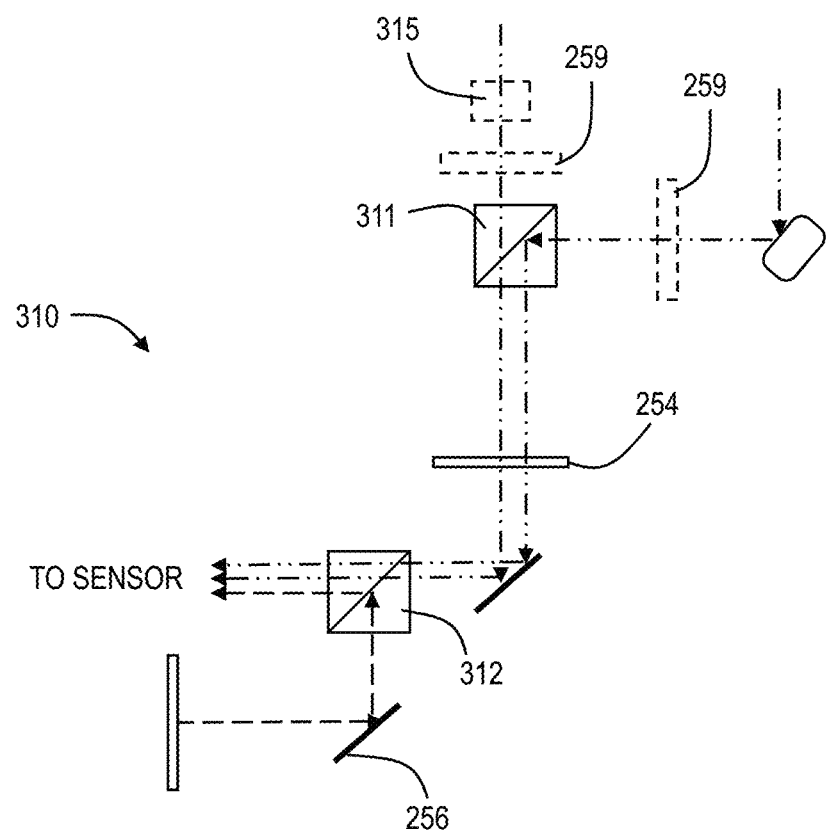
FIG. 13 is a schematic diagram of an illustrative optical collector configured to simultaneously collect sky radiance, water radiance, and reference plaque radiance according to aspects of the present disclosure.

An illustrative sky-water-plaque collector 310 is depicted in FIG. 13. Sky-water-plaque collector 310 is configured to collect light from the sky, from the water, and from a reference plaque substantially simultaneously. Sky-water-plaque collector 310 includes a first optical assembly 311 configured to combine two sources of light (e.g., from the sky and from the plaque, from the sky and from the water, or from the water and from the plaque) into a first light combination, and to transmit the first light combination to a second optical assembly 312 configured to combine the first light combination with a third source of light (e.g., light from a source not included in the first light combination) to produce a second light combination including light from all three sources. In the example depicted in FIG. 13, the first and second optical assemblies comprise beamsplitters, but any suitable combination of optical elements may be included. One or more polarizing elements 315 may be included to polarize light such that it is reflected by, or transmitted by, a polarizing beamsplitter in first optical assembly 311. Additionally, or alternatively, polarizing elements may be configured to polarize light such that it is reflected or transmitted by second optical assembly 312, and/or any other suitable optical component(s). Mirrors and/or polarizing reflectors may be used to steer the first light combination toward second optical assembly 312 and/or to steer the second light combination toward the sensor. Any one or more of the sky light, plaque light, and water light may be independently modulated with a modulation depth, frequency, and/or pattern configured to enable the light from the different sources to be distinguished from each other.

vi. Illustrative Sequential Plaque Collector

Figure 14:
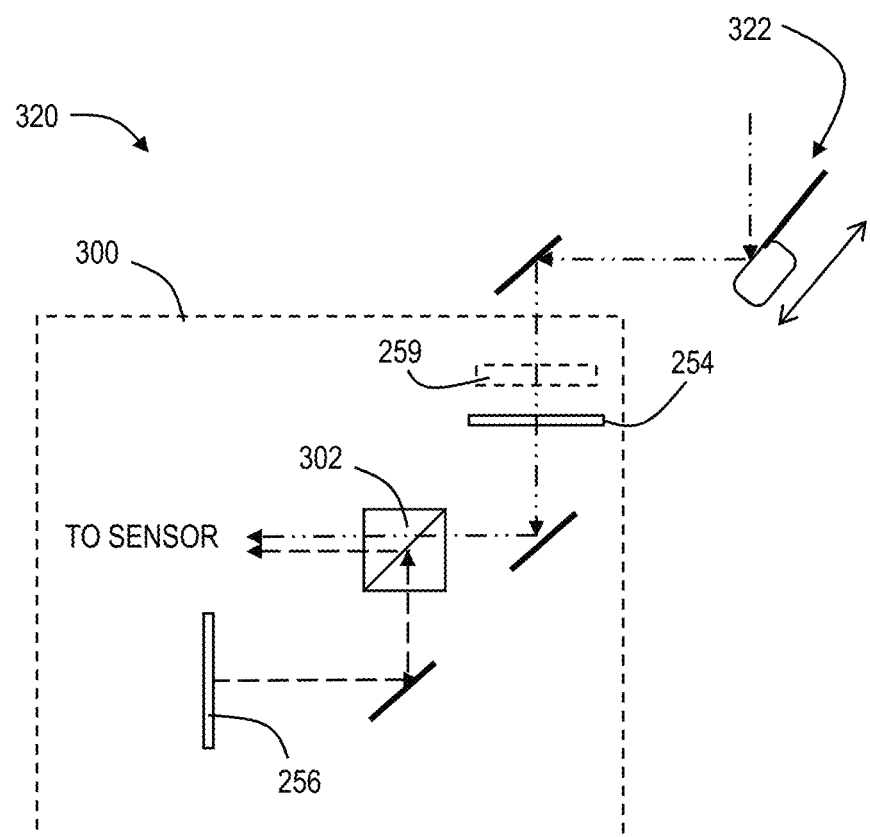
FIG. 14 is a schematic diagram of an illustrative optical collector configured to simultaneously and/or sequentially measure sky radiance, water radiance, and/or reference plaque radiance according to aspects of the present disclosure.

An illustrative sequential plaque collector 320 is depicted in FIG. 14. Sequential plaque collector 320 includes a sky-water collector 250 (e.g., beamsplitter collector 300) and further includes an alternating element 322 configured to selectively direct sky light or plaque light into an entrance aperture of the collector. For example, alternating element 322 may include a reference plaque and a mirror, either or both of which are movable. The mirror may be moved in front of the plaque such that it substantially blocks light reflected by the plaque from entering the entrance aperture and reflects sky light into the entrance aperture, or moved away from the plaque such that light reflected by the plaque may enter the aperture. The mirror and/or the plaque may be disposed on translation stages that are manually movable and/or motorized. The mirror and/or the plaque may be mounted rotatably, such that the mirror may be rotated in front of the plaque for a sky radiance measurement and rotated away from the plaque for a plaque radiance measurement. Water light enters sequential plaque collector 320 through a second entrance aperture (e.g., water-radiance aperture 256) regardless of the position of alternating element 322. A simultaneous measurement of water-radiance and sky-radiance may therefore be followed immediately by a simultaneous measurement of water-radiance and plaque-radiance. The time between the first simultaneous measurement and the second simultaneous measurement is so short (due to the speed at which alternating element 322 may be moved, as well as time characteristics of the associated sensor) that the first and second measurements may be considered nearly simultaneous with each other for many purposes. For example, atmospheric conditions such as cloud cover are likely to change very little between the first and second measurements.

In the example depicted in FIG. 14, alternating element 322 alternately allows sky light or plaque light to enter a first aperture, while water light is never prevented from entering a second aperture. In other examples, alternating element 322 alternately allows water light or plaque light to enter the first aperture, while sky light is never prevented from entering the second aperture.

Alternating element 322 may be added to any suitable sky-water collector 250 (e.g., exterior to the sky-radiance aperture 254 or water radiance aperture 256) to make a sequential plaque collector

E. Illustrative Network of Hyperspectral Sensing Devices

Figure 15:
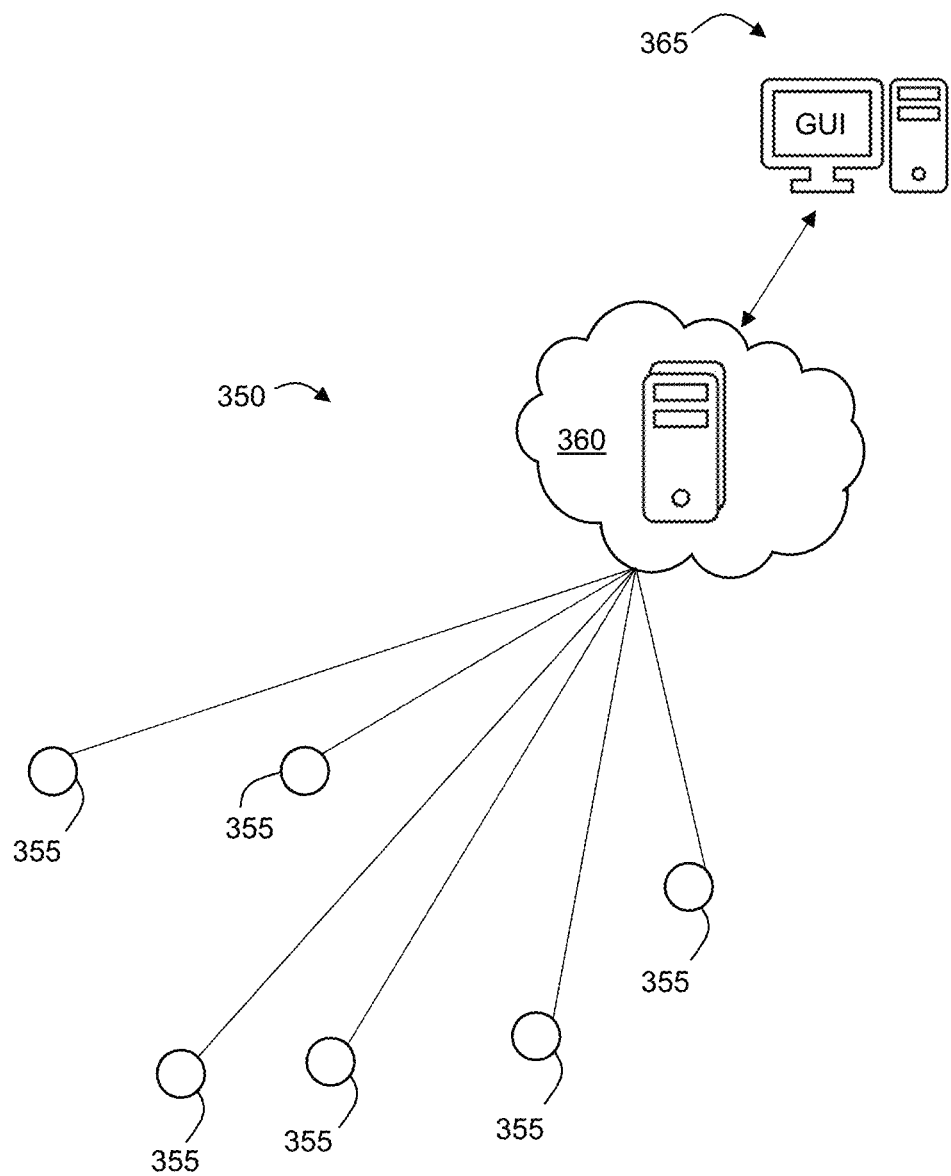
FIG. 15 is a schematic diagram of an illustrative network of hyperspectral sensing devices in accordance with aspects of the present teachings.

With reference to FIG. 15, this section describes an illustrative hyperspectral sensing system 350 in accordance with aspects of the present teachings.

As depicted schematically in FIG. 15, system 350 comprises a plurality of hyperspectral sensing devices 355. Devices 355 may comprise and/or be similar to device 30 and/or any other suitable devices. Devices 355 may be distributed across any suitable area. In some examples, devices 355 are distributed adjacent to, on, and/or in a body of water (e.g., above water, underwater, on coasts, on buoys, on weather stations, and/or in any similar location). Additionally, or alternatively, devices 355 may be distributed on land, on aerial vehicles, on weather balloons, and/or in any suitable location. Each device 355 is configured to acquire hyperspectral data and to transmit the acquired data to a location remote from the device. Although a selected number of devices is shown in FIG. 15, more or fewer devices may be utilized, and system 350 may include different numbers of devices at different times. In some examples, subsets of devices within the system may be collocated.

Each device 355 is configured to communicate with a computer network 360 via a wireless communications module of the device (e.g., input/output hub 80, described above). Computer network 360 may be configured to communicate data (e.g., to transmit data to and/or receive data from) a server 365 and/or any other suitable device. Communication between devices 355 and computer network 360, and/or between the network and server 365, may comprise radio frequency (RF) antenna, GSM (Global System for Mobile Communications)/GPRS (General Packet Radio Service) cellular modem, Bluetooth® wireless technology, WiFi, and/or any other suitable protocol.

Typically, devices 355 are configured for autonomous operation. In this mode, the devices transmit acquired data to server 365 via computer network 360 at selected intervals (e.g., on a predetermined schedule, in response to the acquired data meeting one or more criteria, and/or at any other suitable time). For example, data may be transmitted daily, several times per day, in real-time or near real-time (e.g., every 10-15 minutes), and/or at any other suitable interval.

In some examples, server 365 transmits data and/or instructions to one or more of the devices (e.g., to an input/output hub of a device). These communications from server 365 may include software and/or firmware updates, operating settings (e.g., sample rates, sample intervals, integration times, types of data, etc.), calibration routines, and/or data transfer protocols of the devices. Additionally, or alternatively, server 365 may synchronize clocks of the devices, manage power settings of the devices, and/or trigger specific routines (e.g., calibration).

In some examples, devices 355 are each configured to communicate with one or more of a plurality of different servers using one or more parallel networks.

In examples wherein each device 355 includes two or more sensors (e.g., two or more spectrometers, or at least one spectrometer and at least one auxiliary sensor), any suitable electronics on board the device may be used to operate the sensors and to transmit the acquired data. For example, the device may include a dedicated microcontroller or other processing logic for each of the sensors. Alternatively, a single microcontroller may be configured to control all sensors, or a plurality of the sensors. In some examples, a data processing system on board the device may be configured to control the sensors and/or to control communication with network 360.

In cases wherein data from the two or more sensors is combined, the data may be transmitted to server 365 independently and combined after transmission to reduce power usage of the local electronics module. However, in some cases, data from multiple sensors is combined prior to transmission to reduce transmission bandwidth.

F. Illustrative Method for Sky-Water Measurement

Figure 16:
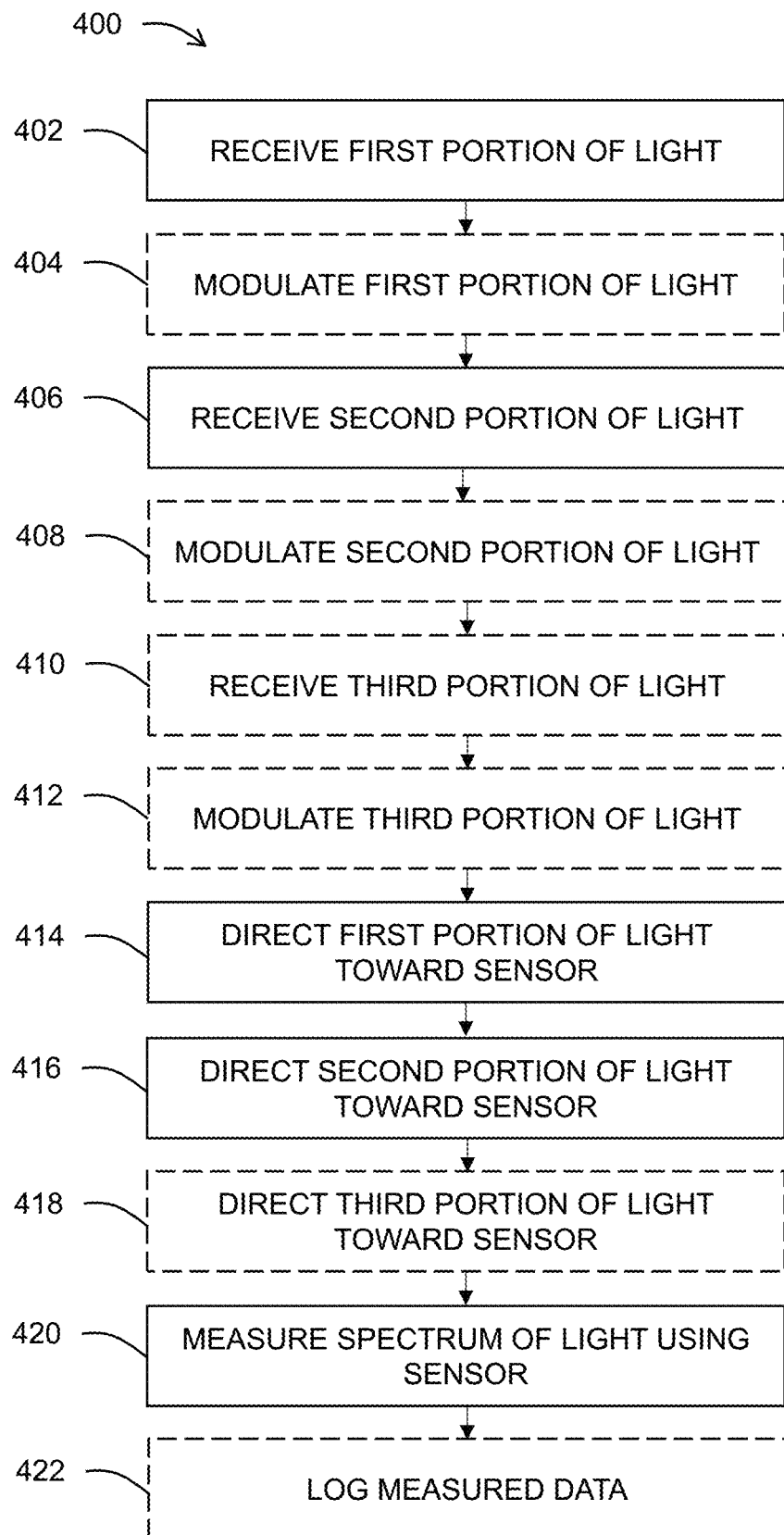
FIG. 16 is a flow diagram depicting steps of an illustrative method for simultaneous measurement of sky radiance and water radiance according to the present teachings.

This section describes steps of an illustrative method 400 for simultaneous or near-simultaneous measurement of a combination of sky radiance, water radiance, and/or plaque radiance; see FIG. 16. Aspects of sky-water collectors 250 may be utilized in the method steps described below. Where appropriate, reference may be made to components and systems that may be used in carrying out each step. These references are for illustration, and are not intended to limit the possible ways of carrying out any particular step of the method.

FIG. 16 is a flowchart illustrating steps performed in an illustrative method, and may not recite the complete process or all steps of the method. Although various steps of method 400 are described below and depicted in FIG. 16, the steps need not necessarily all be performed, and in some cases may be performed simultaneously or in a different order than the order shown.

At step 402, the method includes receiving a first portion of light in an optical collector of a hyperspectral sensing system (e.g., hyperspectral sensing device 30). For example, the first portion of light may be light from the sky above a body of water. The first portion of light may be received via a first entrance aperture of the optical collector.

At step 404, the method optionally includes modulating the first portion of light. For example, the first portion of light may be amplitude-modulated using a chopper wheel.

At step 406, the method includes receiving a second portion of light in the optical collector, e.g., via a second entrance aperture of the optical collector. For example, the second portion of light may be light upwelling from a body of water.

At step 408, the method optionally includes modulating the second portion of light, e.g., using a chopper wheel.

At step 410, the method optionally includes receiving a third portion of light in the optical collector. The third portion of light may be received via a third entrance aperture of the collector. The third portion of light may be light reflected from a reference plaque.

At step 412, the method optionally includes modulating the third portion of light. If more than one of the first, second, and third portions of light are modulated, they are modulated in different patterns. For example, they may be modulated with chopper wheels 260 having openings of different sizes, having blocking portions of different sizes, and/or having different speeds of rotation. The different modulation enables the measurements of the first, second, and third light portions to be distinguished from each other, e.g., as described above with reference to chopper wheel 260.

At step 414, the method includes directing the first portion of light toward a sensor (e.g., toward an entrance aperture of sensor 40 and/or toward an imaging detector such as a CCD or CMOS array). At step 416, the method includes directing the second portion of light toward the sensor. At step 418, the method optionally includes directing the third portion of light, if it is present, toward the sensor. Directing any one of the portions of light toward the sensor may include reflecting the light from a reflective optical element, dispersing the light with a dispersive optical element, and/or diffracting the light with a diffractive optical element. Directing the portions of light toward the sensor may include combining one or more portions of light using a polarizing or nonpolarizing beamsplitter. Combining one or more portions of light using a polarizing beamsplitter may include polarizing at least one of the portions of light (e.g., using a wire-grid polarizer, quarter-wave plate, and/or thin-film polarizer) such that it reflects from the beamsplitter and is combined with at least one portion of light that impinges on the beamsplitter from another direction and is transmitted. In some cases, two portions of light may be combined first and subsequently combined with the third portion of light. In some examples, directing the first, second, and/or third portion of light toward the sensor includes adjusting a position of an optical element, such as a rotatable mirror. In some embodiments, steps 402 and 414 may be performed simultaneously and/or before step 406.

At step 420, the method includes measuring a spectrum of light impinging on the sensor. The impinging light typically includes the first, second, and/or third portions of light directed toward the sensor in steps 414-418. Measuring a spectrum of the light may include using a transducer configured to convert intensity of received light into an electrical voltage or current signal readable by an electronics module. In some examples, measuring a spectrum of the impinging light may include dispersing the impinging light with a dispersive optical element such as a blazed grating, such that spectral components of the impinging light are spatially separated. Measuring the spectrum may further include measuring an intensity of light at a variety of spatial points (e.g., using a CMOS linear array) and converting the spatial points into spectral information.

At step 422, the method optionally includes logging the measured data (e.g., the voltage signals read by the electronics module) in a volatile or nonvolatile storage medium (e.g., a memory) associated with the hyperspectral sensor. Alternatively, or additionally, the measured data may be transmitted to an external device.

G. Illustrative Method for Hyperspectral Measurements Using a Light Source

Figure 17:
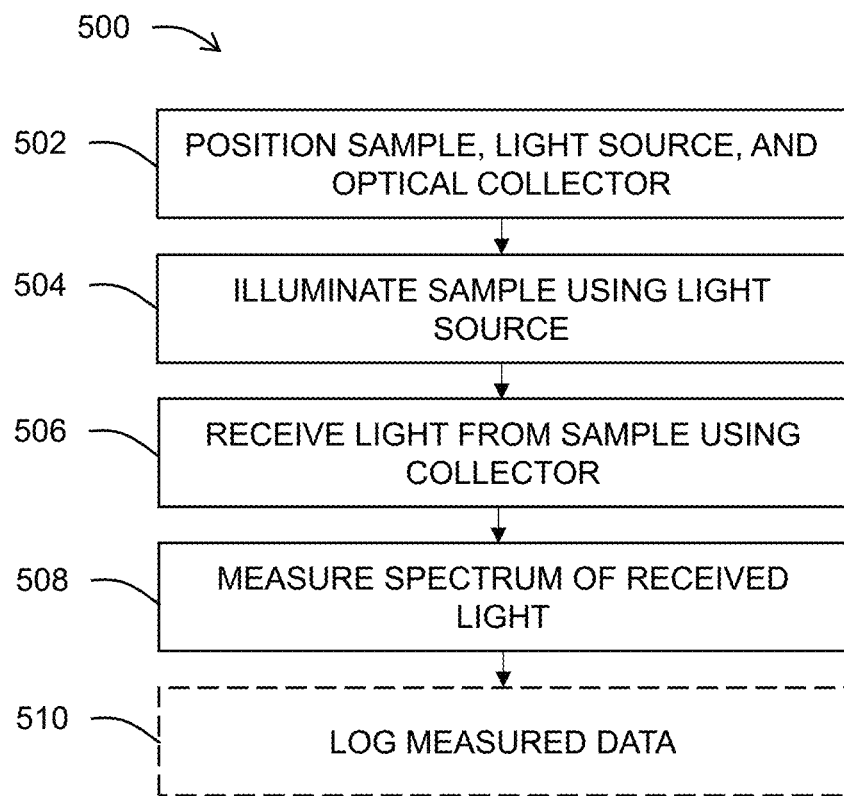
FIG. 17 is a flow diagram depicting steps of an illustrative method for performing fluorescence, scattering, and/

This section describes steps of an illustrative method 500 for hyperspectral measurements of absorption, fluorescence, luminescence, and/or scattering; see FIG. 17. Aspects of hyperspectral sensing device 30 may be utilized in the method steps described below. Where appropriate, reference may be made to components and systems that may be used in carrying out each step. These references are for illustration, and are not intended to limit the possible ways of carrying out any particular step of the method.

FIG. 17 is a flowchart illustrating steps performed in an illustrative method, and may not recite the complete process or all steps of the method. Although various steps of method 500 are described below and depicted in FIG. 17, the steps need not necessarily all be performed, and in some cases may be performed simultaneously or in a different order than the order shown.

At step 502, the method includes positioning a sample, a light source, and an optical collector of a hyperspectral sensing system. The collector may comprise a slit of fixed width, and may further include optical components as discussed elsewhere herein. Positioning the sample, the light source and the collector may include immersing the light source and/or collector in water (e.g., placing the collector and light source underwater). In this case, the hyperspectral measurements are made underwater, and the water may be the sample. In some examples, the sample is between the light source and the collector. In some examples, the light source and the collector form a desired angle with sample, which may be an acute angle (e.g., to enable back-scattering measurements).

In some examples, step 502 includes disposing one or more tagging agents in the sample (e.g., biologically and/or chemically altering the sample by addition of the tagging agents). Tagging agents are configured to bind with specific predetermined substances such as biological cells, sub-cellular structures, sub-sub-cellular structures and/or compounds (e.g., proteins), and to exhibit identifiable wavelength-dependent luminescent and fluorescent signatures (e.g., in response to illumination by a suitable light source). The addition of tagging agents to the sample thus enables the identification of the tagged substances (e.g., a specific cellular species) and/or determination of the abundance, mass, or density of the tagged substance based on the intensity of the fluorescence, the volume of the sample throughout which the tagging agents are distributed, and/or any other suitable factors. Suitable tagging agents may include lanthanides and/or any other suitable reagents.

At step 504, the method includes illuminating the sample with the light source. The light source may be an LED, laser, lamp, and/or any other suitable device configured to emit light. In some examples, the light source is modulated.

At step 506, the method includes receiving light propagating from the sample using the collector. The collector may receive light propagating from the sample along a predetermined direction and/or within a predetermined solid angle. Receiving light propagating from the sample may include receiving light that originated in the light source and was scattered elastically or inelastically from the sample, was reflected from the sample, and/or was transmitted through the sample, and/or may include receiving light that was produced by fluorescence within the sample (e.g., by substances within the sample, by tagging agents within the sample, etc.). The collector may be configured to attenuate and/or block light received directly from the light source.

At step 508, the method includes measuring a spectrum of the received light. Measuring a spectrum of the received light may include directing the light toward a sensor, such as a compact spectrometer, using the collector.

At step 510, the method optionally includes logging the measured data in a memory device of the hyperspectral sensing system.

H. Illustrative Method for Assessing Water Quality

Figure 18:
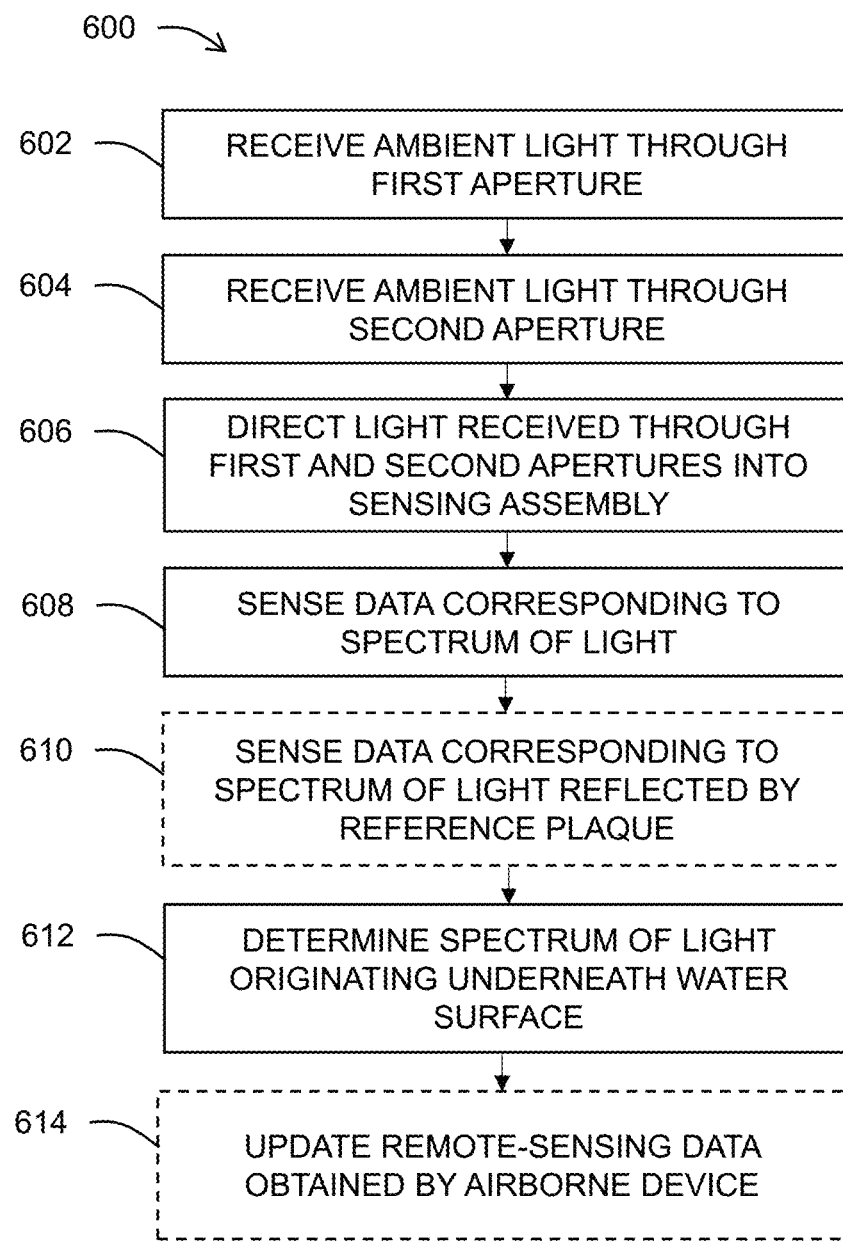
FIG. 18 is a flow diagram depicting steps of an illustrative method for assessing water quality.

This section describes steps of an illustrative method 600 for assessing water quality; see FIG. 18. Aspects of hyperspectral sensing systems and devices described above may be utilized in the method steps described below. Where appropriate, reference may be made to components and systems that may be used in carrying out each step. These references are for illustration, and are not intended to limit the possible ways of carrying out any particular step of the method.

FIG. 18 is a flowchart illustrating steps performed in an illustrative method, and may not recite the complete process or all steps of the method. Although various steps of method 600 are described below and depicted in FIG. 18, the steps need not necessarily all be performed, and in some cases may be performed simultaneously or in a different order than the order shown.

A step 602, the method includes receiving ambient light through a first aperture of a housing of an optical device (e.g., device 30) disposed adjacent a surface of a body of water. The first aperture may be, e.g., the aperture of an optical collector of the device. The first aperture is directed at the surface of the body of water, such that light received through the first aperture includes light reflected from the surface and light passing through the surface from underneath.

At step 604, the method includes receiving ambient light through a second aperture of the housing, the second aperture being directed at the sky. Light received from the second aperture therefore includes light coming from the sky. The second aperture may be, e.g., a second aperture of an optical collector of the device, which may be the same collector that includes the first aperture, or a different collector of the device. Receiving light at step 602 and/or step 604 may include modulating the received light (e.g., to facilitate distinguishing measurements of the light received through the different apertures).

At step 606, the method includes directing light received from the first and second apertures into a sensor assembly disposed within a housing of the device. The light may be directed by any suitable optical assembly. In some examples, the sensor assembly includes a first spectrometer for sensing light received through the first aperture and a second spectrometer for sensing light received through the second aperture. Alternatively, the sensor assembly may comprise only one spectrometer, and light received through either aperture is directed to the same spectrometer. In the latter case, light from the two apertures may be directed simultaneously or sequentially to the common spectrometer (e.g., using aspects of illustrative sky-water collectors describe above).

At step 608, the method includes sensing, using the sensing assembly, data corresponding to a spectrum of the light received from the first and second apertures. The spectrometer(s) of the sensing assembly have sufficient spectral resolution to enable hyperspectral measurements. The data may be sensed simultaneously or sequentially.

At step 610, the method optionally includes sensing data corresponding to a spectrum of light reflected by a reference plaque. As described in Section D, a reference plaque typically comprises a flat, rigid surface having known reflectance properties and configured to reflect incident light diffusely and isotropically (e.g., a Lambertian reflector). Accordingly, with the reference plaque positioned above the surface of the water, a spectrum of light reflected from the sensing plaque may be used to determine wavelength-dependence of the irradiance of downwelling light from the sky in all directions. This may be used to calculate a remote-sensing reflectance (e.g., a measure of how much of the radiance traveling in all downward directions is reflected upward into any direction), and/or any other suitable property. Sensing data corresponding to the spectrum reflected by the reference plaque typically includes receiving data light reflected by the reference plaque through any suitable aperture of the device, including the first or second apertures, and sensing the spectrum using any suitable spectrometer.

At step 612, the method includes determining, based on the sensed data, a spectrum of light originating underneath the surface of the water (e.g., water-leaving light). For example, a remote-sensing reflectance may be calculated based on the following equation:

$$R_{rs} = \frac{(S_T - \rho(\theta)S_s)}{\pi(S_{ref}/R_{ref})}.$$

In this equation, $S_T$ represents a measured signal of light received through the first aperture (the water-directed aperture), $S_S$ represents a measured signal of light received through the second aperture (the sky-directed aperture), $S_{ref}$ represents an average measured signal from a reference plaque, and $R_{ref}$ represents a reflectivity of the plaque. The measured signal from the second aperture is multiplied by $\rho(\theta)$, a proportionality factor relating radiance measured when the detector views the sky to the reflected sky radiance measured when the detector views the sea surface. The value of this proportionality factor may depend on wind speed and direction, detector field of view, and sky radiance distribution. The proportionality factor may be a Mobley proportionality factor. The factor of $\pi$ converts the reflected plaque radiance to an irradiance (e.g., it converts direction-dependent data to direction-independent data). Alternatively, or additionally, calculating the remote-sensing reflectance may include determining a surface correction of the radiance received through the sky-directed aperture based on a bidirectional reflectance distribution function.

As described above in Section D, the remote-sensing reflectance obtained by this calculation comprises information about a spectrum of light originating underneath the surface of the water (e.g., the water-leaving light); specifically, the remote-sensing reflectance is a wavelength-dependent ratio of radiance leaving the water in a particular viewing direction to the total sky irradiance just above the water's surface. Accordingly, the remote-sensing reflectance may be used to infer information about, e.g., biological, chemical, and/or geological constituents in the water containing substances (e.g., pigments) that alter optical properties of the water. In other examples, a spectrum of light originating underneath the surface of the water may be obtained in another way.

As described above, in some examples light received through the first and second apertures are measured by a same spectrometer, possibly simultaneously. In other words, a signal measured by the spectrometer includes contributions from light received through the first aperture and contributions from light received through the second aperture. In these examples, determining a spectrum of water-leaving light at step 612 includes distinguishing the two contributions (e.g., to obtain the signals $S_T$ and $S_S$ described above). Typically, distinguishing the two contributions is facilitated by modulating the light received through one or both apertures (e.g., prior to measuring the light with the spectrometer), as described above with reference to steps 602 and 604. As an example, if the light is modulated such that light from one aperture is periodically blocked (or otherwise prevented from reaching the spectrometer), then the two contributions may be distinguished by subtracting a spectrum obtained when light from one aperture is blocked from a spectrum obtained when neither aperture is blocked. For example, the spectrum of light received through the sky-directed aperture could be subtracted from the combined spectrum of light received through both apertures. Typically, light received through one aperture (usually the sky-directed aperture) has a higher intensity than light received through the other aperture, and subtracting the higher of the two signals from the combined signal may increase the accuracy of the calculation. The subtraction may be performed by hardware and/or software.

Additionally, or alternatively, the contributions from the sky-directed aperture and the water-directed aperture may be separated using differential spectral and/or a filter configured to selectively reject and/or transmit one or both contributions based on a frequency and/or phase of modulation. In some cases, a lock-in amplifier may be used to isolate one of the contributions, based on the frequency and/or phase of modulation. In some cases, light received through one or both apertures is wavelength-modulated (e.g., using a movable dispersing element) to facilitate separation of the two signals using a spectral filter. Based on known properties of the wavelength modulator, the measured wavelength-modulated spectra can be corrected. These techniques may be implemented in hardware and/or software.

Any processing performed to distinguish the two contributions may be performed on board the device or on an external data processing system (or other suitable device).

At step 614, the method optionally includes using the sensed data and/or the determined spectrum of water-leaving light to update remote-sensing data of the same body of water obtained by an airborne device. Remote-sensing data (e.g., wavelength-dependent reflectances of ground and/or bodies of water) obtained by an airborne device (e.g., a satellite, aircraft, unmanned aerial vehicle, and/or the like) commonly includes inaccuracies due to the passage of the sensed light through the atmosphere. Clouds, turbulence, and/or other aspects of the atmosphere may distort the light as it travels from the ground to the airborne device, such that the measured light does not accurately represent optical properties of the ground and/or water being surveyed. Additionally, an airborne device positioned high above the surface of the Earth may have a lower temporal, spatial, and/or spectral resolution than an instrument disposed nearer the ground. Accordingly, the remote-sensing data obtained by the airborne device may be cross-referenced with the spectrum obtained at step 612 in order to correct inaccuracies in the remote-sensing data. Corrections obtained in this manner may be extrapolated to remote-sensing data obtained in areas where no other data is available.

As an alternative, or addition, to the above method, a plurality of optical devices may be disposed adjacent the surface of the body of water, with each device having a respective aperture pointed at approximately a same portion of the surface. The devices, or collecting optics of the devices, are positioned such that each of the respective apertures is directed at the surface at a different orientation (e.g., at different angles relative to azimuth and/or zenith, resulting in a different viewing geometry). Data corresponding to a spectrum of light received through each aperture is sensed by sensing assemblies of the devices. Based on the sensed data, a spectrum of light originating underneath the surface of the water is determined. For example, a total downwelling irradiance from the sky may be collected (e.g., using a diffuser/cosine corrector and/or reflectance plaque), and the water-leaving radiance may be calculated based on data sensed by the surface-directed devices and the total downwelling irradiance. Calculating the water-leaving radiance may include, e.g., modeling a bidirectional reflectance distribution function for the surface of the water. The bidirectional reflectance distribution function may be determined based on, e.g., the solar zenith and azimuth (determined by measurements, date and time and geographic position of measurement, and/or any other suitable factors), device zenith and azimuth, field of view, surface roughness (based e.g. on wind speed), and a suitable model of light behavior at the water-sky interface. A suitable model of light behavior at the water-sky interface may include, e.g. transmittance and reflectance amplitudes, phase, and polarization at the interface based on Fresnel equations, Maxwell's equations, and/or any other suitable model.

Based on the bidirectional reflectance distribution function of the surface, the amount of surface-reflected radiance that each device is theoretically expected to measure may be calculated. This theoretical prediction may be compared to the radiance actually measured by each device, which includes both surface-reflected radiance and water-leaving radiance. Based on the theoretical prediction, the differences in signals measured by the devices viewing the same portion of the surface from different directions may be used to obtain an estimate of the contribution of the surface-reflected radiances to the measured signals. Based on this estimate, the water-leaving radiance corresponding to each device is calculated (e.g., by subtracting the estimated surface-reflection contributions from the measured signals). The remote-sensing reflectance corresponding to each device may be obtained by dividing the water-leaving radiance by the total sky irradiance.

Alternatively, the water-leaving radiance may be calculated without an explicit model of the bidirectional reflectance distribution function for the surface of the water. For example, the relationship between the upwelling radiances measured by the plurality of devices may be estimated (based on, e.g., the measurement angles of the devices), and this relationship may be used to estimate the water-leaving radiance. Estimating the relationship between the measured upwelling radiances may include using a linear or nonlinear fit on the measured data and/or a simulation predicting the radiances. In some examples, at least two of the devices are configured to have viewing angles at which the water-leaving radiances are predicted (e.g., by angular symmetry at a given time of day and location) to be substantially equal. This may simplify the calculation of the relationship between the measured radiances.

According to this method, no sky-directed aperture is required, though one may optionally be used.

I. Illustrative Method for Acquiring Hyperspectral Data Above Water and Underwater This section describes steps of an illustrative method 700 for acquiring hyperspectral data above water and underwater using a single device; see FIG. 19. Aspects of hyperspectral sensing systems and devices described above (e.g. device 30) may be utilized in the method steps described below. Where appropriate, reference may be made to components and systems that may be used in carrying out each step. These references are for illustration, and are not intended to limit the possible ways of carrying out any particular step of the method.

Figure 19:
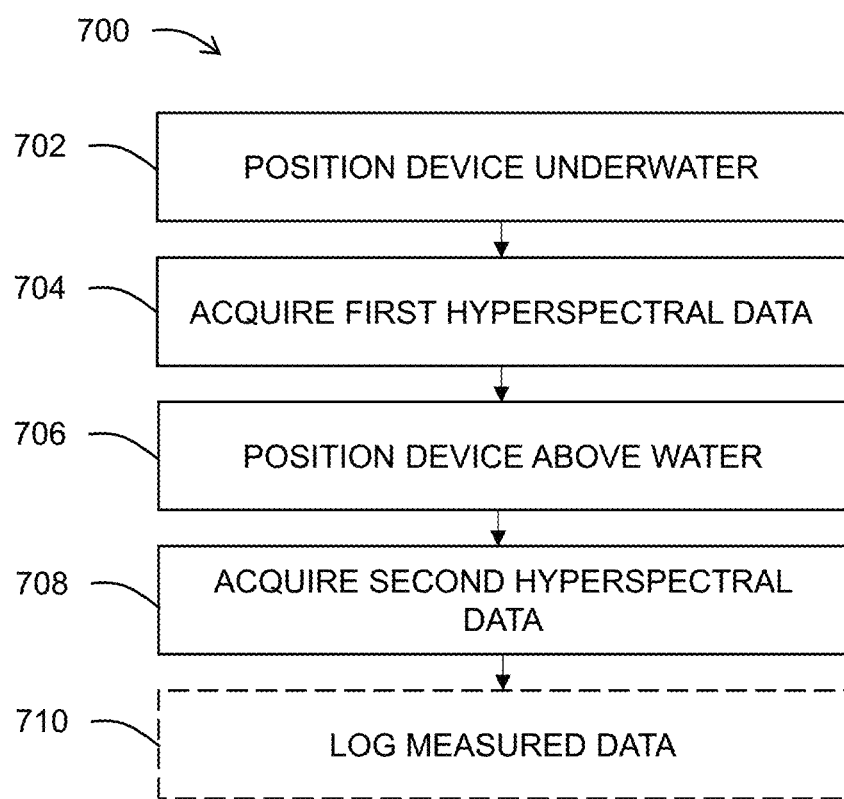
FIG. 19 is a flow diagram depicting steps of an illustrative method for acquiring hyperspectral data above water and underwater.

FIG. 19 is a flowchart illustrating steps performed in an illustrative method, and may not recite the complete process or all steps of the method. Although various steps of method 700 are described below and depicted in FIG. 19, the steps need not necessarily all be performed, and in some cases may be performed simultaneously or in a different order than the order shown.

At step 702, the method includes positioning a hyperspectral sensing device underwater. Typically, the entire device is immersed in water (e.g., in a body of water such as an ocean), but in some examples, only a portion of the device is immersed (e.g., the optical collector). The device typically includes a wireless communications module and a power supply. Accordingly, when the device is deployed underwater, it need not be connected by a power cable or data cable to another platform or device (e.g., a ship on the water's surface). This reduces the risk that another platform or device will cast a shadow over the area being sampled, or otherwise interfere with the sample.

At step 704, the method includes acquiring a first portion of hyperspectral data underwater. Acquiring the data typically includes collecting light (e.g., ambient light) with a collector of the device and transferring the collected light to a suitable sensor of the device (e.g., a compact spectrometer). Acquiring the data may further include scanning a region or object of interest (e.g., by adjustment of the collector to collect light from different spatial areas or directions, by transporting the device on an underwater vehicle such that the collector collects light from different areas, and/or the like).

At step 706, the method includes positioning the device above water (e.g., moving the device from an underwater position to an above-water position). The above-water position may comprise a ship, buoy, platform, shore, or other suitable location near the water. Alternatively, the above-water position may be located far from the water in which the device had been immersed. In some examples, the above-water position is in the air (e.g., with the device mounted on an unmanned aerial vehicle or other suitable device).

At step 708, the method includes acquiring a second portion of hyperspectral data above water. Acquiring the data includes collecting light and may include scanning a region or object of interest, as described above with reference to step 704. The sensor of the device is configured to acquire data both underwater and above-water. For example, the sensor is sufficiently sensitive to acquire data with a suitable signal-to-noise ratio in underwater environments, which are typically associated with low light levels, and is also capable of acquiring data in bright above-water environments (e.g., the sensor has a high dynamic range). In some examples, one or more settings of the sensor and/or collector are changed for the acquisition of the second portion of data. For example, an integration time, sampling rate, aperture size, filter selection, and/or other suitable parameter may be different when the device acquires data above water compared to when the device acquires data underwater. Such a parameter may be varied automatically by a controller on board the device (e.g., in response to measuring a higher light level, lower external pressure, and/or other suitable indication) and/or may be changed by a user (e.g., a user communicating with the controller via an external computer). In some cases, the collector used underwater is replaced with a different collector when the device is removed from the water, but the same spectrometer is used in both environments.

At step 710, the method optionally includes logging the acquired first and second data portions on a memory store of the device.

In some examples, steps 706-708 are performed prior to steps 702-704. That is, the above-water measurements may be performed prior to immersing the device in water and performing the underwater measurements.

In some examples, the steps of positioning the device above water and positioning the device underwater include deliberately moving the device to selected locations. Alternatively, these steps may occur automatically as the device is immersed in water due to changing environmental conditions. For example, the device may disposed on a platform that is sometimes immersed in water (e.g., due to changing tides).

J. Illustrative Embedded Microcontroller Architecture

Figure 20:
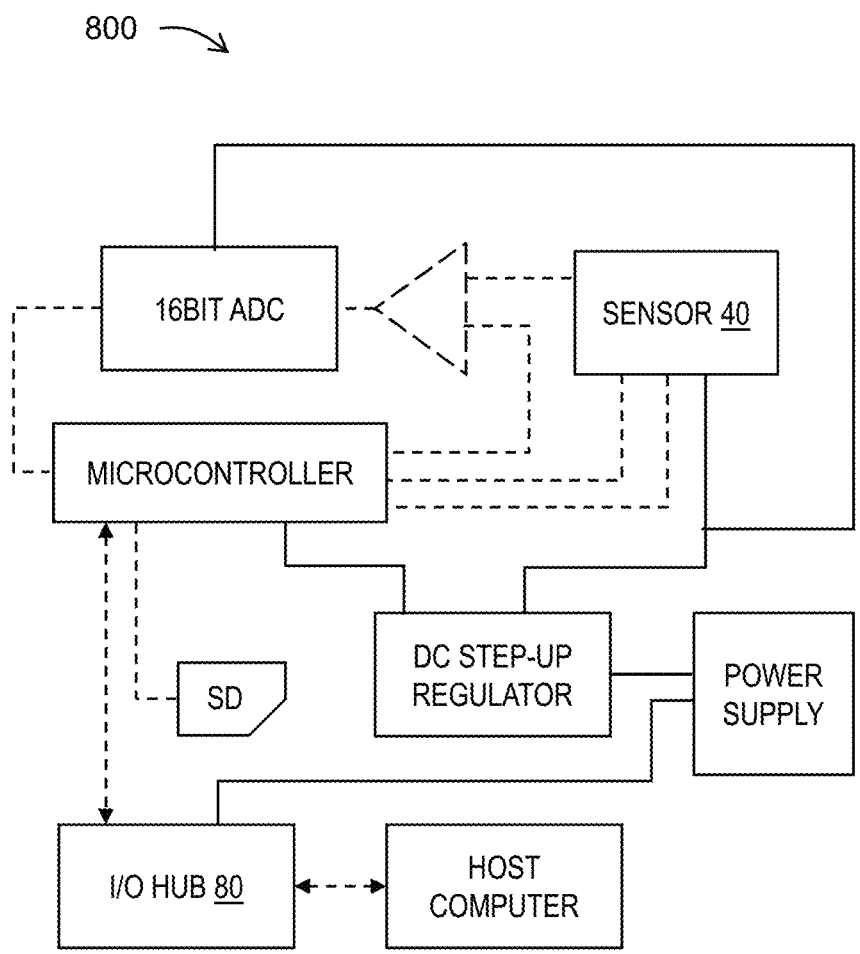
FIG. 20 is a schematic diagram depicting an illustrative electronics module of a hyperspectral sensing system, in accordance with aspects of the present teachings.

In some examples, electronics module 70 comprises an embedded-systems microcontroller architecture 800. Power supply 90 and/or input/output hub 80 may be integrated into embedded microcontroller architecture 800. An example embedded microcontroller architecture 800 is depicted schematically in FIG. 20.

Using embedded microcontroller architecture 800, hyperspectral sensing device 30 is powered by a DC regulator from a power supply such as an internal battery or an auxiliary power supply, which provides stable power output independent of the changes in the electrical load, and can be provided via USB, inductive charging or external power source. The power supply is configured to meet the demand of the on-board sensors, and therefore a DC step-up voltage amplifier can be used to increase the output of a low-voltage battery (such as 3.7V LiPoly/LiIon) to an operating voltage of, for example, 5V. A DC-DC converter can also be used to lower and regulate a higher-voltage DC power supply (for example 12V) to an operating voltage of 5V, or to multiple voltage levels selected for optimal operation of various sensors and devices. The power is supplied to the microcontroller unit (MCU), sensors, external analog-to-digital converter circuitry as well as input-output (I/O) hub 80.

Although many micro-controller units feature an integrated multi-channel analog-to-digital converter (ADC), one or multiple external function-specific ADCs may be used to address the needs to process analog signals at high sample rates, in some cases in excess of 1-million samples-per-second (SPS) and/or with increased digital precision, e.g., in the range of 10-bit to 16-bit, or 18-bit, or higher. The analog to digital conversion can be pre-amplified and conditioned using any number of gain-amplification, signal-conditioning, and/or electronics filtering stages, or can be referenced to differential signals to boost the signal while suppressing electronic noise. The digitized video signal from the ADC (from either the hyper-spectral or other analog sensors) are ingested and processed by the MCU and stored in memory, such as a flash memory storage device, e.g., an SD or microSD card, or other memory device for later transfer to an external host computer for additional levels of data processing. The data may additionally be directly up-linked in real-time (while measurements are progressing, or at regularly scheduled intervals) to land-based systems through a wireless or wired device communication port, such as USB, WiFi, Bluetooth, Bluetooth LE, GSM, Iridium, etc.

The micro-controller (MCU) supplies the operating voltage, clock and trigger timing signals to the sensor 40. The supplied clock rate is used to operate the sensor acquisition and output (video) data rate, while the trigger signal is used to initiate and end the optical integration (or image acquisition), based on the control input from the MCU. The trigger control operation can be programmed via software or firmware and may be adjustable for example based on processing of the camera video output. Additionally, if multiple hyper-spectral sensors are used, the trigger signal may be set to sequentially or synchronously acquire data from multiple sensors.

In some example triggering schemes, the integration time is determined real-time via software control based on inputs from external signals supplied to the MCU from auxiliary sensors 50. This may for example include temperature, pressure, GPS location, compass heading, tilt/yaw, etc., whereby the sensor would be set to trigger data acquisitions, when specific conditions for these parameters are met. For example, the data acquisitions may be set to trigger operating at specific depth intervals or at specific sensor tilt angles. The trigger and clock rates may also be modulated simply to budget the data output rates or manage power consumption during longer operating deployments. Also, the trigger may be activated at specific times in concert with a specific light source 60 or engagement of an optical filter in collector 35 to enable an absorbance, back-scattering or fluorescence measurement.

In some examples, particularly if data or computational bandwidth limitation exceed the capability of a single MCU, a more powerful micro-processing unit (MPU) or multiple micro-controller units may be used to control and operate driving circuitry for different subsystems, for example for adjustments of the collector aperture, pointing/steering control of the instrument, image stabilization, or fusing of multi-sensor inputs.

K. Illustrative Data Processing System

Figure 21:
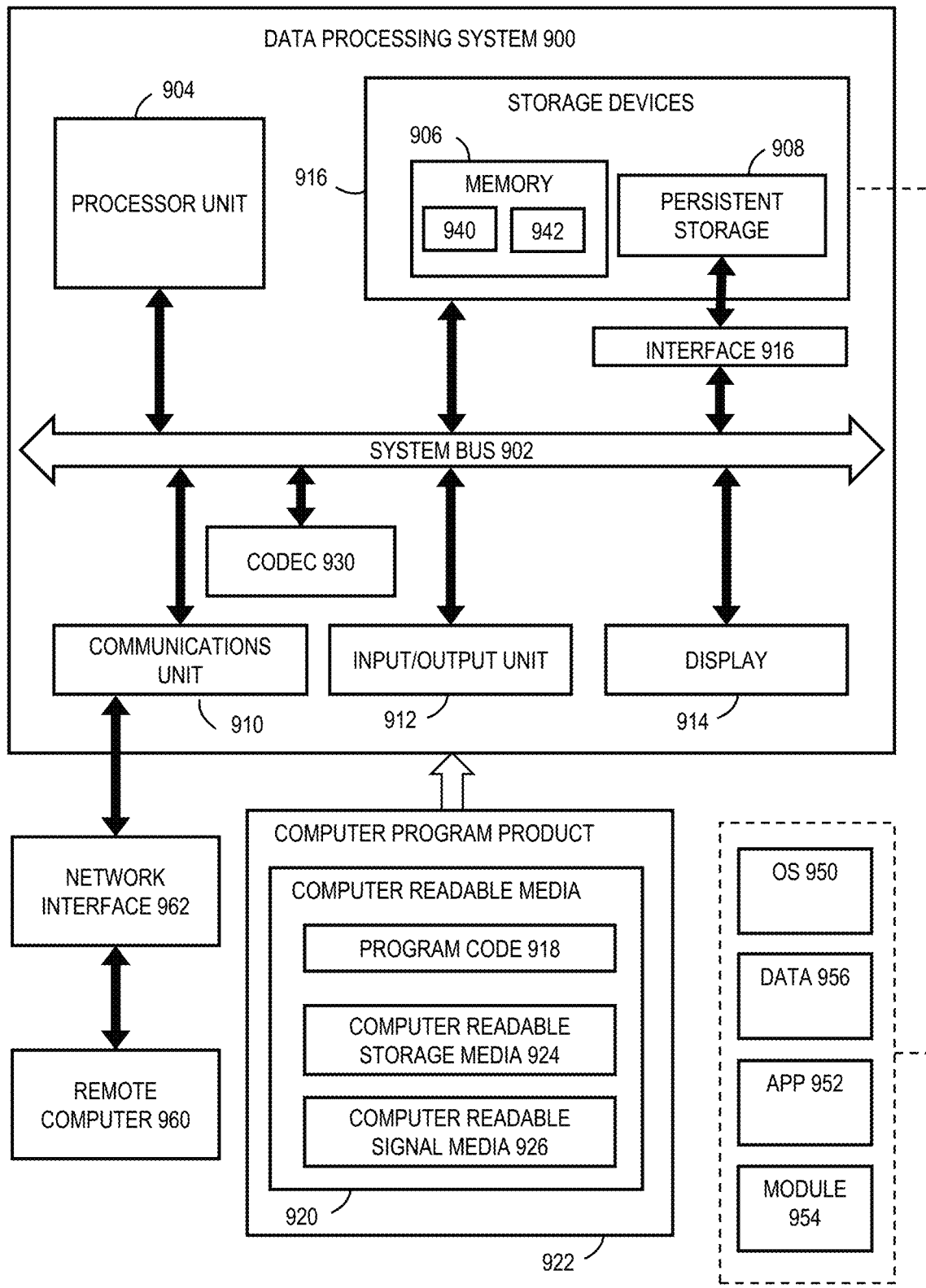
FIG. 21 is a schematic diagram of an illustrative data processing system in accordance with aspects of the present teachings.

As shown in FIG. 21, this example describes a data processing system 900 (also referred to as a computer, computing system, and/or computer system) in accordance with aspects of the present disclosure. Data processing system 900 is an illustrative data processing system suitable for implementing aspects of the hyperspectral sensing systems and devices described above. More specifically, in some examples, devices that are embodiments of data processing systems (e.g., smartphones, tablets, personal computers) may be included on a hyperspectral sensing device (e.g., as part of an on-board electronics module) and used to control acquisition of data by a sensor of the device and/or data communications between the device and a remote server. Additionally, or alternatively, devices that are embodiments of data processing systems may be used to communicate with hyperspectral sensing device(s) to, e.g., program the devices, retrieve data from the devices, etc.

In this illustrative example, data processing system 900 includes a system bus 902 (also referred to as communications framework). System bus 902 may provide communications between a processor unit 904 (also referred to as a processor or processors), a memory 906, a persistent storage 908, a communications unit 910, an input/output (I/O) unit 912, a codec 930, and/or a display 914. Memory 906, persistent storage 908, communications unit 910, input/output (I/O) unit 912, display 914, and codec 930 are examples of resources that may be accessible by processor unit 904 via system bus 902.

Processor unit 904 serves to run instructions that may be loaded into memory 906. Processor unit 904 may comprise a number of processors, a multi-processor core, and/or a particular type of processor or processors (e.g., a central processing unit (CPU), graphics processing unit (GPU), etc.), depending on the particular implementation. Further, processor unit 904 may be implemented using a number of heterogeneous processor systems in which a main processor is present with secondary processors on a single chip. As another illustrative example, processor unit 904 may be a symmetric multi-processor system containing multiple processors of the same type.

Memory 906 and persistent storage 908 are examples of storage devices 916. A storage device may include any suitable hardware capable of storing information (e.g., digital information), such as data, program code in functional form, and/or other suitable information, either on a temporary basis or a permanent basis.

Storage devices 916 also may be referred to as computer-readable storage devices or computer-readable media. Memory 906 may include a volatile storage memory 940 and a non-volatile memory 942. In some examples, a basic input/output system (BIOS), containing the basic routines to transfer information between elements within the data processing system 900, such as during start-up, may be stored in non-volatile memory 942. Persistent storage 908 may take various forms, depending on the particular implementation.

Persistent storage 908 may contain one or more components or devices. For example, persistent storage 908 may include one or more devices such as a magnetic disk drive (also referred to as a hard disk drive or HDD), solid state disk (SSD), floppy disk drive, tape drive, Jaz drive, Zip drive, flash memory card, memory stick, and/or the like, or any combination of these. One or more of these devices may be removable and/or portable, e.g., a removable hard drive. Persistent storage 908 may include one or more storage media separately or in combination with other storage media, including an optical disk drive such as a compact disk ROM device (CD-ROM), CD recordable drive (CD-R Drive), CD rewritable drive (CD-RW Drive), and/or a digital versatile disk ROM drive (DVD-ROM). To facilitate connection of the persistent storage devices 908 to system bus 902, a removable or non-removable interface is typically used, such as interface 928. Input/output (I/O) unit 912 allows for input and output of data with other devices that may be connected to data processing system 900 (i.e., input devices and output devices). For example, input device 932 may include one or more pointing and/or information-input devices such as a keyboard, a mouse, a trackball, stylus, touch pad or touch screen, microphone, joystick, game pad, satellite dish, scanner, TV tuner card, digital camera, digital video camera, web camera, and/or the like. These and other input devices may connect to processor unit 904 through system bus 902 via interface port(s) 936. Interface port(s)

936 may include, for example, a serial port, a parallel port, a game port, and/or a universal serial bus (USB).

Output devices 934 may use some of the same types of ports, and in some cases the same actual ports, as input device(s) 932. For example, a USB port may be used to provide input to data processing system 900 and to output information from data processing system 900 to an output device 934. Output adapter 938 is provided to illustrate that there are some output devices 934 (e.g., monitors, speakers, and printers, among others) which require special adapters. Output adapters 938 may include, e.g. video and sounds cards that provide a means of connection between the output device 934 and system bus 902. Other devices and/or systems of devices may provide both input and output capabilities, such as remote computer(s) 960. Display 914 may include any suitable human-machine interface or other mechanism configured to display information to a user, e.g., a CRT, LED, or LCD monitor or screen, etc.

Communications unit 910 refers to any suitable hardware and/or software employed to provide for communications with other data processing systems or devices. While communication unit 910 is shown inside data processing system 900, it may in some examples be at least partially external to data processing system 900. Communications unit 910 may include internal and external technologies, e.g., modems (including regular telephone grade modems, cable modems, and DSL modems), ISDN adapters, and/or wired and wireless Ethernet cards, hubs, routers, etc. Data processing system 900 may operate in a networked environment, using logical connections to one or more remote computers 960. A remote computer(s) 960 may include a personal computer (PC), a server, a router, a network PC, a workstation, a microprocessor-based appliance, a peer device, a smart phone, a tablet, another network note, and/or the like. Remote computer(s) 960 typically include many of the elements described relative to data processing system 900. Remote computer(s) 960 may be logically connected to data processing system 900 through a network interface 962 which is connected to data processing system 900 via communications unit 910. Network interface 962 encompasses wired and/or wireless communication networks, such as local-area networks (LAN), wide-area networks (WAN), and cellular networks. LAN technologies may include Fiber Distributed Data Interface (FDDI), Copper Distributed Data Interface (CDDI), Ethernet, Token Ring, and/or the like. WAN technologies include point-to-point links, circuit switching networks (e.g., Integrated Services Digital networks (ISDN) and variations thereon), packet switching networks, and Digital Subscriber Lines (DSL).

Codec 930 may include an encoder, a decoder, or both, comprising hardware, software, or a combination of hardware and software. Codec 930 may include any suitable device and/or software configured to encode, compress, and/or encrypt a data stream or signal for transmission and storage, and to decode the data stream or signal by decoding, decompressing, and/or decrypting the data stream or signal (e.g., for playback or editing of a video). Although codec 930 is depicted as a separate component, codec 930 may be contained or implemented in memory, e.g., non-volatile memory 942.

Non-volatile memory 942 may include read only memory (ROM), programmable ROM (PROM), electrically programmable ROM (EPROM), electrically erasable programmable ROM (EEPROM), flash memory, and/or the like, or any combination of these. Volatile memory 940 may include random access memory (RAM), which may act as external cache memory. RAM may comprise static RAM (SRAM), dynamic RAM (DRAM), synchronous DRAM (SDRAM), double data rate SDRAM (DDR SDRAM), enhanced SDRAM (ESDRAM), and/or the like, or any combination of these.

Instructions for the operating system, applications, and/or programs may be located in storage devices 916, which are in communication with processor unit 904 through system bus 902. In these illustrative examples, the instructions are in a functional form in persistent storage 908. These instructions may be loaded into memory 906 for execution by processor unit 904. Processes of one or more embodiments of the present disclosure may be performed by processor unit 904 using computer-implemented instructions, which may be located in a memory, such as memory 906.

These instructions are referred to as program instructions, program code, computer usable program code, or computer-readable program code executed by a processor in processor unit 904. The program code in the different embodiments may be embodied on different physical or computer-readable storage media, such as memory 906 or persistent storage 908. Program code 918 may be located in a functional form on computer-readable media 920 that is selectively removable and may be loaded onto or transferred to data processing system 900 for execution by processor unit 904. Program code 918 and computer-readable media 920 form computer program product 922 in these examples. In one example, computer-readable media 920 may comprise computer-readable storage media 924 or computer-readable signal media 926.

Computer-readable storage media 924 may include, for example, an optical or magnetic disk that is inserted or placed into a drive or other device that is part of persistent storage 908 for transfer onto a storage device, such as a hard drive, that is part of persistent storage 908. Computer-readable storage media 924 also may take the form of a persistent storage, such as a hard drive, a thumb drive, or a flash memory, that is connected to data processing system 900. In some instances, computer-readable storage media 924 may not be removable from data processing system 900.

In these examples, computer-readable storage media 924 is a non-transitory, physical or tangible storage device used to store program code 918 rather than a medium that propagates or transmits program code 918. Computer-readable storage media 924 is also referred to as a computer-readable tangible storage device or a computer-readable physical storage device. In other words, computer-readable storage media 924 is media that can be touched by a person.

Alternatively, program code 918 may be transferred to data processing system 900, e.g., remotely over a network, using computer-readable signal media 926. Computer-readable signal media 926 may be, for example, a propagated data signal containing program code 918. For example, computer-readable signal media 926 may be an electromagnetic signal, an optical signal, and/or any other suitable type of signal. These signals may be transmitted over communications links, such as wireless communications links, optical fiber cable, coaxial cable, a wire, and/or any other suitable type of communications link. In other words, the communications link and/or the connection may be physical or wireless in the illustrative examples.

In some illustrative embodiments, program code 918 may be downloaded over a network to persistent storage 908 from another device or data processing system through computer-readable signal media 926 for use within data processing system 900. For instance, program code stored in a computer-readable storage medium in a server data processing system may be downloaded over a network from the server to data processing system 900. The computer providing program code 918 may be a server computer, a client computer, or some other device capable of storing and transmitting program code 918.

In some examples, program code 918 may comprise an operating system (OS) 950. Operating system 950, which may be stored on persistent storage 908, controls and allocates resources of data processing system 900. One or more applications 952 take advantage of the operating system's management of resources via program modules 954, and program data 956 stored on storage devices 916. OS 950 may include any suitable software system configured to manage and expose hardware resources of computer 900 for sharing and use by applications 952. In some examples, OS 950 provides application programming interfaces (APIs) that facilitate connection of different type of hardware and/or provide applications 952 access to hardware and OS services. In some examples, certain applications 952 may provide further services for use by other applications 952, e.g., as is the case with so-called "middleware." Aspects of present disclosure may be implemented with respect to various operating systems or combinations of operating systems.

The different components illustrated for data processing system 900 are not meant to provide architectural limitations to the manner in which different embodiments may be implemented. One or more embodiments of the present disclosure may be implemented in a data processing system that includes fewer components or includes components in addition to and/or in place of those illustrated for computer 900. Other components shown in FIG. 21 can be varied from the examples depicted. Different embodiments may be implemented using any hardware device or system capable of running program code. As one example, data processing system 900 may include organic components integrated with inorganic components and/or may be comprised entirely of organic components (excluding a human being). For example, a storage device may be comprised of an organic semiconductor.

In some examples, processor unit 904 may take the form of a hardware unit having hardware circuits that are specifically manufactured or configured for a particular use, or to produce a particular outcome or progress. This type of hardware may perform operations without needing program code 918 to be loaded into a memory from a storage device to be configured to perform the operations. For example, processor unit 904 may be a circuit system, an application specific integrated circuit (ASIC), a programmable logic device, or some other suitable type of hardware configured (e.g., preconfigured or reconfigured) to perform a number of operations. With a programmable logic device, for example, the device is configured to perform the number of operations and may be reconfigured at a later time. Examples of programmable logic devices include, a programmable logic array, a field programmable logic array, a field programmable gate array (FPGA), and other suitable hardware devices. With this type of implementation, executable instructions (e.g., program code 918) may be implemented as hardware, e.g., by specifying an FPGA configuration using a hardware description language (HDL) and then using a resulting binary file to (re)configure the FPGA.

In another example, data processing system 900 may be implemented as an FPGA-based (or in some cases ASIC-based), dedicated-purpose set of state machines (e.g., Finite State Machines (FSM)), which may allow critical tasks to be isolated and run on custom hardware. Whereas a processor such as a CPU can be described as a shared-use, general purpose state machine that executes instructions provided to it, FPGA-based state machine(s) are constructed for a special purpose, and may execute hardware-coded logic without sharing resources. Such systems are often utilized for safety-related and mission-critical tasks.

In still another illustrative example, processor unit 904 may be implemented using a combination of processors found in computers and hardware units. Processor unit 904 may have a number of hardware units and a number of processors that are configured to run program code 918. With this depicted example, some of the processes may be implemented in the number of hardware units, while other processes may be implemented in the number of processors.

In another example, system bus 902 may comprise one or more buses, such as a system bus or an input/output bus. Of course, the bus system may be implemented using any suitable type of architecture that provides for a transfer of data between different components or devices attached to the bus system. System bus 902 may include several types of bus structure(s) including memory bus or memory controller, a peripheral bus or external bus, and/or a local bus using any variety of available bus architectures (e.g., Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire (IEEE 1394), and Small Computer Systems Interface (SCSI)).

Additionally, communications unit 910 may include a number of devices that transmit data, receive data, or both transmit and receive data. Communications unit 910 may be, for example, a modem or a network adapter, two network adapters, or some combination thereof. Further, a memory may be, for example, memory 906, or a cache, such as that found in an interface and memory controller hub that may be present in system bus 902.

L. Illustrative Distributed Data Processing System

Figure 22:
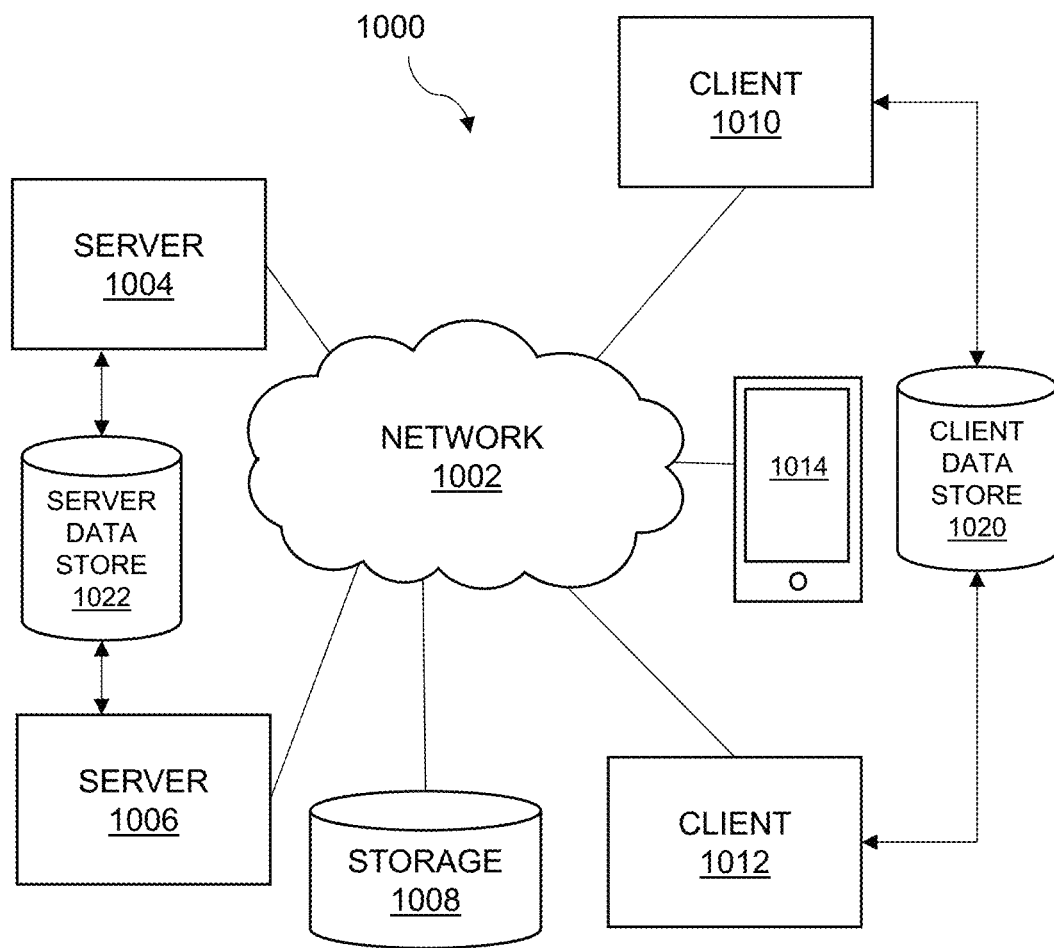
FIG. 22 is a schematic diagram of an illustrative distributed data processing system in accordance with aspects of the present teachings.

As shown in FIG. 22, this example describes a general network data processing system 1000, interchangeably termed a computer network, a network system, a distributed data processing system, or a distributed network, aspects of which may be used in conjunction with illustrative embodiments of hyperspectral sensing devices and/or systems. For example, hyperspectral sensing devices may transmit acquired data via a network and/or may receive instructions via a network. Network 1000 is an example of a network that may be used for data communication within hyperspectral sensing system 350.

It should be appreciated that FIG. 22 is provided as an illustration of one implementation and is not intended to imply any limitation with regard to environments in which different embodiments may be implemented. Many modifications to the depicted environment may be made.

Network system 1000 is a network of devices (e.g., computers), each of which may be an example of data processing system 900, and other components. Network data processing system 1000 may include network 1002, which is a medium configured to provide communications links between various devices and computers connected within network data processing system 1000. Network 1002 may include connections such as wired or wireless communication links, fiber optic cables, and/or any other suitable medium for transmitting and/or communicating data between network devices, or any combination thereof.

In the depicted example, a first network device 1004 and a second network device 1006 connect to network 1002, as do one or more computer-readable memories or storage devices 1008. Network devices 1004 and 1006 are each examples of data processing system 900, described above. In the depicted example, devices 1004 and 1006 are shown as server computers, which are in communication with one or more server data store(s) 1022 that may be employed to store information local to server computers 1004 and 1006, among others. However, network devices may include, without limitation, one or more personal computers, mobile computing devices such as personal digital assistants (PDAs), tablets, and smartphones, handheld gaming devices, wearable devices, tablet computers, routers, switches, voice gates, servers, electronic storage devices, imaging devices, media players, and/or other networked-enabled tools that may perform a mechanical or other function. These network devices may be interconnected through wired, wireless, optical, and other appropriate communication links.

In addition, client electronic devices 1010 and 1012 and/or a client smart device 1014, may connect to network 1002. Each of these devices is an example of data processing system 900, described above regarding FIG. 21. Client electronic devices 1010, 1012, and 1014 may include, for example, one or more personal computers, network computers, and/or mobile computing devices such as personal digital assistants (PDAs), smart phones, handheld gaming devices, wearable devices, and/or tablet computers, and the like. In the depicted example, server 1004 provides information, such as boot files, operating system images, and applications to one or more of client electronic devices 1010, 1012, and 1014. Client electronic devices 1010, 1012, and 1014 may be referred to as "clients" in the context of their relationship to a server such as server computer 1004. Client devices may be in communication with one or more client data store(s) 1020, which may be employed to store information local to the clients (e,g., cookie(s) and/or associated contextual information). Network data processing system 1000 may include more or fewer servers and/or clients (or no servers or clients), as well as other devices not shown.

In some examples, first client electric device 1010 may transfer an encoded file to server 1004. Server 1004 can store the file, decode the file, and/or transmit the file to second client electric device 1012. In some examples, first client electric device 1010 may transfer an uncompressed file to server 1004 and server 1004 may compress the file. In some examples, server 1004 may encode text, audio, and/or video information, and transmit the information via network 1002 to one or more clients.

Client smart device 1014 may include any suitable portable electronic device capable of wireless communications and execution of software, such as a smartphone or a tablet. Generally speaking, the term "smartphone" may describe any suitable portable electronic device configured to perform functions of a computer, typically having a touchscreen interface, Internet access, and an operating system capable of running downloaded applications. In addition to making phone calls (e.g., over a cellular network), smartphones may be capable of sending and receiving emails, texts, and multimedia messages, accessing the Internet, and/or functioning as a web browser. Smart devices (e.g., smartphones) may also include features of other known electronic devices, such as a media player, personal digital assistant, digital camera, video camera, and/or global positioning system. Smart devices (e.g., smartphones) may be capable of connecting with other smart devices, computers, or electronic devices wirelessly, such as through near field communications (NFC), BLUETOOTH®, WiFi, or mobile broadband networks. Wireless connectively may be established among smart devices, smartphones, computers, and/or other devices to form a mobile network where information can be exchanged.

Data and program code located in system 1000 may be stored in or on a computer-readable storage medium, such as network-connected storage device 1008 and/or a persistent storage 908 of one of the network computers, as described above, and may be downloaded to a data processing system or other device for use. For example, program code may be stored on a computer-readable storage medium on server computer 1004 and downloaded to client 1010 over network 1002, for use on client 1010. In some examples, client data store 1020 and server data store 1022 reside on one or more storage devices 1008 and/or 908.

Network data processing system 1000 may be implemented as one or more of different types of networks. For example, system 1000 may include an intranet, a local area network (LAN), a wide area network (WAN), or a personal area network (PAN). In some examples, network data processing system 1000 includes the Internet, with network 1002 representing a worldwide collection of networks and gateways that use the transmission control protocol/Internet protocol (TCP/IP) suite of protocols to communicate with one another. At the heart of the Internet is a backbone of high-speed data communication lines between major nodes or host computers. Thousands of commercial, governmental, educational and other computer systems may be utilized to route data and messages. In some examples, network 1002 may be referred to as a "cloud." In those examples, each server 1004 may be referred to as a cloud computing node, and client electronic devices may be referred to as cloud consumers, or the like. FIG. 22 is intended as an example, and not as an architectural limitation for any illustrative embodiments.

M. Illustrative Combinations and Additional Examples

This section describes additional aspects and features of hyperspectral sensing systems, presented without limitation as a series of paragraphs, some or all of which may be alphanumerically designated for clarity and efficiency. Each of these paragraphs can be combined with one or more other paragraphs, and/or with disclosure from elsewhere in this application, including the materials incorporated by reference in the Cross-References, in any suitable manner. Some of the paragraphs below expressly refer to and further limit other paragraphs, providing without limitation examples of some of the suitable combinations.

A0. A hyperspectral sensing system comprising an image sensor configured to measure an intensity of each of a plurality of spectral bands of impinging light; an optical collector configured to direct light to impinge on the image sensor; and an electronics module configured to store data corresponding to the intensity measured by the image sensor.

A1. The system of A0, wherein the optical collector includes a first aperture and a second aperture each configured to accept light; and an optical director configured to direct light accepted by the first aperture and light accepted by the second aperture to impinge on the image sensor.

A2. The system of A0, further comprising a light source, and wherein the optical collector is mounted slidably on a rail such that an angle subtended by the light source, the optical collector, and a sample object may be selectively adjusted.

B0. A hyperspectral sensing system comprising a compact spectrometer; a collector having a first aperture disposed in a first plane and configured to receive light, a second aperture disposed in a second plane and configured to receive light, and an optical director configured to direct the light received by the first and second apertures to the compact spectrometer; wherein the first and second planes are non-planar relative to each other.

B1. The system of B0, further comprising a modulator having a plurality of openings and a plurality of blocking portions, wherein the blocking portions are configured to block light.

C0. A method for simultaneously performing hyperspectral measurements on light from two sources, the method comprising receiving a first portion of light via a first entrance aperture of an optical collector; receiving a second portion of light via a second entrance aperture of the optical collector; directing the first portion of light to impinge on a sensor configured to a measure wavelength-dependent intensity of impinging light; and directing the second portion of light to impinge on the sensor.

D0. A method for performing a hyperspectral fluorescence measurement, the method comprising positioning a sample, a light source, and an optical collector such that the sample, in response to illumination from the light source, emits light in a direction receivable by the optical collector; illuminating the sample using the light source; receiving light emitted by the sample using the optical collector; and measuring respective intensities of a plurality of spectral components of the received light using a sensor associated with the collector.

D1. The method of D0, wherein positioning the sample, the light source, and the optical collector includes disposing the sample and the optical collector underwater.

D2. The method of any one of D0-D1, further comprising disposing within the sample one or more tagging agents each configured to bind with a predetermined substance and to emit an identifiable wavelength-dependent fluorescence in response to illumination by the light source.

D3. The method of D2, wherein at least one of the one or more tagging agents comprises a lanthanide-based tag.

E0. Further aspects of an illustrative hyperspectral sensing system are described below:

The collector consisting of a fixed aperture of 0.01 to 5 mm in between the sample and the sensor.

The collector consisting of ground-glass (fused silica/SiO2) diffuser with an entrance aperture (diffuser on sample side and aperture on sensor side).

The collector consisting of an 8 degree numerical aperture SiO2 plano convex lens between the sample and detector located at the primary focal plane.

The sensor comprising one or more dispersive elements such as prisms, waveguides, diffractive optical elements, etc.

Use of 'multi-spectral' (i.e. discrete wavelength band) sensors with higher number of bands (~10-30 bands)

Use of light-sensitive detectors (i.e. photodiodes) and optical color-filters or band-pass filters Actuation, scanning or movement entire system (sensor+collector) to acquire image of scene larger than single FOV (pixel). In some examples, the collector could remain stationary relative to sensor.

Use of image stabilization technology to additional improve acuity of image obtained on a scanning or moving platform.

Use of local storage solutions beyond non-volatile memory, flash memory, SD/micro-SD cards, etc.

Use of other data transfer technologies, as applicable, microwave, laser, etc. communication to carry out the data streaming/logging functionality.

Use of an interface for live-viewing and/or capturing the measured output (or some analysis of the measured output) on a separate handheld device (e.g. cell-phone, tablet, computer, etc.). This can be done via wired (serial, parallel) or wireless interface.

A hyperspectral sensing device mounted on a buoy, weather station, weather balloon, unmanned aerial vehicle, unmanned underwater vehicle, watercraft, aircraft, satellite, automobile, and/or any other suitable platform.

F0. An autonomous optical sensing device comprising a first spectrometer including a sensing element; an optical system configured to direct ambient light incident from a first direction onto the sensing element of the first spectrometer; and a first controller coupled to the first spectrometer and configured to automatically trigger data acquisition by the first spectrometer at selected intervals; wherein the first spectrometer and the optical system are at least partially encased in a common housing.

F1. The device of F0, wherein the optical system is further configured to direct ambient light incident from a second direction onto the sensing element of the first spectrometer.

F2. The device of F1, further comprising an optical modulator at least partially encased in the common housing, the optical modulator configured to modulate the ambient light incident from the second direction.

F3. The device of any one of F1-F2, further comprising an optical polarizer at least partially encased in the common housing, the optical polarizer configured to polarize the ambient light incident from the second direction.

F3.5 The device of F3, wherein the optical polarizer comprises a circular polarizer.

F4. The device of any one of F0-F3.5, wherein the optical system comprises a first lens assembly having a first value of a selected optical characteristic.

F5. The device of F4, wherein the first lens assembly is interchangeable with a second lens assembly having a second value of the selected optical characteristic.

F6. The device of any one of F4-F5, wherein the optical characteristic is a field of view.

F7. The device of any one of F0-F6, further comprising a second spectrometer at least partially encased in the common housing, wherein the optical system is further configured to direct ambient light incident from a second direction onto a sensing element of the second spectrometer.

F8. The device of F7, further comprising a second controller configured to automatically trigger data acquisition by the second spectrometer at selected intervals and to control transmission of data to a remote server by an onboard data processing system.

F9. The device of F8, wherein the second controller is configured to wake the data processing system from a standby mode at predetermined intervals.

F10. The device of any one of F0-F9, further comprising an optical homogenizer configured to homogenize light incident from the first direction.

F11. The device of any one of F0-F10, further comprising a photovoltaic panel configured to provide electrical power to the first controller and the first spectrometer.

F12. The device of any one of F0-F11, wherein the spectral resolution of the first spectrometer is 20 nanometers or better.

F13. The device of any one of F0-F12, further comprising at least one sensor usable for calibrating the first spectrometer.

F14. The device of F13, wherein the at least one sensor comprises a temperature sensor.

F15. A plurality of the devices of any one of F0-F14, wherein each device is in communication with a distributed computer network.

G0. A method of assessing water quality, the method comprising receiving ambient light through a first aperture of a housing of an optical device disposed adjacent a surface of a body of water, the first aperture being directed at the surface of the body of water, wherein the light received through the first aperture includes light reflected from the surface and light passing through the surface from underneath; receiving ambient light through a second aperture of the housing, the second aperture being directed at the sky, wherein the light received through the second aperture includes light coming from the sky; directing the light received through the first and second apertures into a sensing assembly disposed within the housing; sensing, using the sensing assembly, data corresponding to a spectrum of the light received through the first and second apertures; and determining, based on the sensed data, a spectrum of light originating underneath the surface of the water.

G1. The method of G0, wherein the sensing assembly comprises a first spectrometer and a second spectrometer, and directing the light received from the first and second apertures into the sensing assembly includes directing the light received through the first aperture into the first spectrometer and directing the light received through the second aperture into the second spectrometer.

G2. The method of G0, wherein the sensing assembly comprises a spectrometer, and directing the light received through the first and second apertures into the sensing assembly includes directing the light received through the first and second apertures into the spectrometer.

G3. The method of any one of G0-G2, further comprising updating, using the recorded data, remote-sensing data of the same body of water obtained by an airborne device.

G4. The method of any one of G0-G3, wherein determining the spectrum of light originating underneath the surface of the water includes using a Mobley surface correction.

G5. The method of any one of G0-G4, wherein determining the spectrum of light originating underneath the surface of the water includes using a bidirectional reflectance distribution function.

H0. A method of assessing water quality, the method comprising receiving ambient light through a first aperture of a first optical device disposed adjacent a surface of a body of water, the first aperture being directed at the surface of the body of water at a first orientation; receiving ambient light through a second aperture of a second optical device disposed adjacent the surface, the second aperture being directed at the surface at a second orientation, wherein the light received through the first and second apertures includes light reflected from the surface and light passing through the surface from underneath; directing the light received through the first aperture into a first sensing assembly of the first device; directing the light received through the second aperture into a second sensing assembly of the second device; sensing, using the first and second sensing assemblies, data corresponding to respective spectra of the light received through the first and second apertures; detecting a total downwelling sky irradiance; and determining, based on the sensed data and the detected total downwelling sky irradiance, a spectrum of light originating underneath the surface of the water.

H1. The method of H0, wherein detecting the total downwelling sky irradiance includes using a cosine corrector.

H2. The method of any one of H0-H1, wherein the total downwelling sky irradiance is detected using the first optical device.

H3. The method of any one of H0-H1, wherein the total downwelling irradiance is detected using a third optical device.

H4. The method of any one of H0-H3, wherein the first and second orientations are each defined by a respective azimuth angle and a respective zenith angle.

H5. The method of any one of H0-H3, wherein determining the spectrum of light originating under the water includes calculating a bidirectional reflectance distribution function (BRDF) of the surface of the water; estimating, using the BRDF, the contribution of the light reflected from the surface to the data sensed by each of the sensing assemblies; and correcting the sensed data based on the estimated contributions.

H6. The method of any one of H0-H3, wherein determining the spectrum of light originating under the water includes estimating a relationship between the data sensed by each of the sensing assemblies and determining the spectrum based on the estimated relationship.

H7. The method of H6, wherein the first and second orientations are selected such that radiances of light received through the first and second apertures are approximately equal.

Advantages, Features, and Benefits

The different embodiments and examples of a hyperspectral sensing system described herein provide several advantages over known solutions for acquiring hyperspectral data of aquatic, aerial, and/or terrestrial environments. For example, illustrative embodiments and examples described herein allow a compact, low-weight hyperspectral sensing system having dimensions suitable for deploying on an autonomous vehicle, a remotely operated vehicle, and/or an unmanned aerial vehicle.

Additionally, and among other benefits, illustrative embodiments and examples described herein allow a hyperspectral sensing device that can be deployed autonomously, without power cables or data cables.

Additionally, and among other benefits, illustrative embodiments and examples described herein allow a hyperspectral sensing device that is relatively insensitive to vibrations (e.g., due to use of a compact spectrometer).

Additionally, and among other benefits, illustrative embodiments and examples described herein allow a hyperspectral sensing device to be constructed using a relatively inexpensive compact spectrometer, enabling a network of hyperspectral sensing devices to be deployed at relatively low overall cost.

Additionally, and among other benefits, illustrative embodiments and examples described herein allow a simultaneous or near-simultaneous measurement of sky radiance, upwelling water radiance, and optionally radiance of light reflected from a reference plaque. The ability to make these measurements simultaneously or nearly simultaneously increases the accuracy and precision of the measurements and any quantities inferred from the measurements, such as remote-sensing reflectance.

Additionally, and among other benefits, illustrative embodiments and examples described herein allow hyperspectral measurements in underwater environments, above-water environments, and aerial environments using the same hyperspectral sensing device, which may enable consistency among measurements performed in these different environments. Additionally, the ability to perform measurements in these different environments using just one device decreases the amount of equipment that must be transported to measurement sites (e.g., carried on watercraft, buoys, drones, and/or manually carried by personnel).

Additionally, and among other benefits, illustrative embodiments and examples described herein allow hyperspectral measurements to be made using a device having a wider dynamic range than known hyperspectral sensors, such that a single device is configured to acquire hyperspectral data when deployed underwater and when deployed above water.

Additionally, and among other benefits, illustrative embodiments and examples described herein allow a hyperspectral sensing system to autonomously trigger data collection or adjust measurement parameters based on sensed data such as temperature, pressure, time, location, light levels, salinity, etc.

Additionally, and among other benefits, illustrative embodiments and examples described herein allow collection optics on a hyperspectral sensing system to be adjusted and/or replaced without adjustment to any sensors (e.g., spectrometers).

Additionally, and among other benefits, illustrative embodiments and examples described herein allow hyperspectral measurements of fluorescence, scattering, and/or absorption.

No known system or device can perform these functions. However, not all embodiments and examples described herein provide the same advantages or the same degree of advantage.

CONCLUSION

The disclosure set forth above may encompass multiple distinct examples with independent utility. Although each of these has been disclosed in its preferred form(s), the specific embodiments thereof as disclosed and illustrated herein are not to be considered in a limiting sense, because numerous variations are possible. To the extent that section headings are used within this disclosure, such headings are for organizational purposes only. The subject matter of the disclosure includes all novel and nonobvious combinations and subcombinations of the various elements, features, functions, and/or properties disclosed herein. The following claims particularly point out certain combinations and subcombinations regarded as novel and nonobvious. Other combinations and subcombinations of features, functions, elements, and/or properties may be claimed in applications claiming priority from this or a related application. Such claims, whether broader, narrower, equal, or different in scope to the original claims, also are regarded as included within the subject matter of the present disclosure.

What is claimed is:

1. An autonomous optical sensing device comprising:
a first spectrometer including a sensing element and a dispersive element;
an optical system including an optical director configured to direct ambient light incident from a first direction and ambient light incident from a second direction onto the dispersive element of the first spectrometer, the second direction being nonparallel to the first direction; and
a first controller coupled to the first spectrometer and configured to automatically trigger data acquisition by the first spectrometer at selected intervals;
wherein the first spectrometer and the optical system are at least partially encased in a common housing.

2. The device of claim 1, further comprising an optical modulator at least partially encased in the common housing, the optical modulator configured to modulate the ambient light incident from the second direction.

3. The device of claim 1, further comprising an optical polarizer at least partially encased in the common housing, the optical polarizer configured to polarize the ambient light incident from the second direction.

4. The device of claim 1, wherein the optical system comprises a first lens assembly having a first value of a selected optical characteristic, and wherein the first lens assembly is interchangeable with a second lens assembly having a second value of the selected optical characteristic.

5. The device of claim 4, wherein the optical characteristic is a field of view.

6. The device of claim 1, further comprising a second spectrometer at least partially encased in the common housing, wherein the optical director is further configured to direct ambient light incident from a second direction onto a sensing element of the second spectrometer.

7. The device of claim 6, further comprising a second controller configured to automatically trigger data acquisition by the second spectrometer at selected intervals and to control transmission of data to a remote server by an onboard data processing system.

8. The device of claim 7, wherein the second controller is configured to wake the data processing system from a standby mode at predetermined intervals.

9. The device of claim 1, wherein the first spectrometer has a spectral domain including a range of 300 nm to 900 nm.

10. The device of claim 1, wherein the first controller is configured to automatically enable data acquisition by the first spectrometer in response to detection, by a second sensing element, of an intensity of ambient light above a threshold level.

11. The device of claim 10, wherein the first controller is further configured to automatically disable data acquisition by the first spectrometer in response to detection, by the second sensing element, of an intensity of ambient light below the threshold level.

12. The device of claim 1, wherein the light incident from the first direction is received through a first aperture of the device and the light incident from the second direction is received through a second aperture of the device, wherein the first aperture lies in a first plane and the second aperture lies in a second plane, and the first and second planes are noncoplanar.

13. An autonomous hyperspectral sensing device comprising:
a housing having a first aperture configured to receive ambient light from a first direction and a second aperture configured to receive ambient light from a second direction different from the first direction;
a spectrometer disposed within the housing, the spectrometer including a sensing element, a spectrometer body having an input slit, and an optical element disposed within the spectrometer body and configured to direct light received through the input slit toward the sensing element in wavelength-dependent directions;

an optical system disposed within the housing and configured to direct light received through the first aperture and light received through the second aperture to the input slit;

an electronic controller disposed within the housing and configured to automatically trigger data acquisition by the spectrometer; and an optical modulator configured to modulate an amplitude of the light received through the second aperture before the light received through the second aperture is received at the input slit.

14. The device of claim 13, wherein the optical element of the spectrometer comprises a grating attached to an inner wall of the spectrometer body.

15. The device of claim 13, wherein the spectrometer has a spectral domain including a range of 300 nm to 900 nm.

16. The device of claim 13, further comprising a transmitter disposed at least partially within the housing, and wherein the electronic controller is further configured to control the transmitter to transmit data acquired by the spectrometer to a remote device.

17. The device of claim 13, wherein the optical modulator is disposed within the housing.

18. An autonomous hyperspectral sensing device comprising:

a housing having a first aperture configured to receive ambient light from a first direction;

a spectrometer disposed within the housing, the spectrometer including a first sensing element, a spectrometer body having an input slit, and an optical element disposed within the spectrometer body and configured to direct light received through the input slit toward the first sensing element in wavelength-dependent directions;

an optical system disposed within the housing and configured to direct light received through the first aperture to the input slit; and an electronic controller disposed within the housing and configured to automatically trigger data acquisition by the spectrometer in response to detection, by a second sensing element, of an intensity of ambient light above a threshold level.

19. The device of claim 18, wherein the electronic controller is further configured to automatically disable data acquisition by the spectrometer in response to detection, by the second sensing element, of an intensity of ambient light below the threshold level.

* * * * *